United States Patent
Cassily

(10) Patent No.: US 7,122,004 B1
(45) Date of Patent: Oct. 17, 2006

(54) METHOD AND APPARATUS OF ENHANCING LEARNING CAPACITY

(75) Inventor: James F Cassily, Grand Rapids, MI (US)

(73) Assignee: Interactive Metronome, Inc., Weston, FL (US)

( * ) Notice: Subject to any disclaimer, the term of this patent is extended or adjusted under 35 U.S.C. 154(b) by 438 days.

(21) Appl. No.: 10/048,510

(22) PCT Filed: Aug. 11, 2000

(86) PCT No.: PCT/US00/22160

§ 371 (c)(1),
(2), (4) Date: Jan. 30, 2002

(87) PCT Pub. No.: WO01/12059

PCT Pub. Date: Feb. 22, 2001

Related U.S. Application Data

(60) Provisional application No. 60/189,091, filed on Mar. 14, 2000, provisional application No. 60/229,361, filed on Aug. 13, 1999, and provisional application No. 60/219,321, filed on Aug. 13, 1999.

(51) Int. Cl.
*A61B 5/00* (2006.01)

(52) U.S. Cl. .................. 600/300; 128/905; 434/258; 340/825.19

(58) Field of Classification Search ......... 600/300–301; 128/892–898, 905, 920; 434/236–238, 258, 434/116

See application file for complete search history.

(56) References Cited

U.S. PATENT DOCUMENTS 3,498,169 A    3/1970   Golian 3,771,407 A    11/1973  Leonard
3,905,269 A    9/1975   Doerksen et al.

(Continued)

FOREIGN PATENT DOCUMENTS

WO        WO 9214229         8/1992

OTHER PUBLICATIONS

Paper entitled "Improving Student Motor Integration by Use of an Interactive Metronome™," presented at the Annual Meeting of the American Educational Research Assoc., Mar. 24, 1997, by Paul M. Stemmer, Jr.
Clinical Guide entitled "T.O.V.A.® Test of Variables of Attention," published in 1996, by Lawrence Greenberg.
Paper entitled "Keyboard Magazine Review, Nov. '90," Jeanius Electronics Russian Dragon.

*Primary Examiner*—Max F. Hindenburg
*Assistant Examiner*—Michael C Astorino
(74) *Attorney, Agent, or Firm*—Van Dyke, Gardner, Linn, & Burkhart, LLP

(57) ABSTRACT

A method and apparatus for enhancing a user's learning capacity includes generating a reference signal having occurrences separated by time intervals and receiving from a user a manipulation of a trigger. A temporal relationship is determined between user manipulation of the trigger and occurrence of the reference signal. A guidance signal is generated that is a function of the temporal relationship and is, at least occasionally, presented to the user. A visual image may be displayed that is varying in appearance as a function of user manipulation of the trigger. The guide signal may be withheld for user manipulations of the trigger that are within a particular range that encompasses an occurrence of the reference signal. A direction signal may be generated that indicates a desired user manipulation of the trigger relative to the reference signal. The trigger may be adapted to be manipulated by a young child user.

82 Claims, 14 Drawing Sheets

U.S. PATENT DOCUMENTS

| | | | | |
|---|---|---|---|---|
| 3,919,915 | A | 11/1975 | Isbell | |
| 3,942,516 | A | 3/1976 | Glynn et al. | |
| 4,024,789 | A | 5/1977 | Humphrey et al. | |
| 4,078,469 | A | 3/1978 | Calvin | |
| 4,089,246 | A | 5/1978 | Kooker | |
| 4,120,229 | A | 10/1978 | Ota | |
| 4,202,244 | A | 5/1980 | Gutshall | |
| 4,322,744 | A | 3/1982 | Stanton | |
| 4,325,697 | A | 4/1982 | Regan et al. | |
| 4,364,299 | A | 12/1982 | Nakada et al. | |
| 4,392,830 | A | 7/1983 | Salzman et al. | |
| 4,406,208 | A | 9/1983 | Nazer | |
| 4,432,266 | A | 2/1984 | Nakada | |
| 4,437,381 | A | 3/1984 | Chen | |
| 4,484,507 | A | 11/1984 | Nakada et al. | |
| 4,630,518 | A | 12/1986 | Usami | |
| 4,651,145 | A | 3/1987 | Sutter | |
| 4,651,612 | A | 3/1987 | Matsumoto | |
| 4,736,751 | A | 4/1988 | Gevins et al. | |
| 4,883,067 | A | 11/1989 | Knispel et al. | |
| 4,919,030 | A | 4/1990 | Perron, III | |
| 4,919,143 | A | 4/1990 | Ayers | |
| 4,928,704 | A | 5/1990 | Hardt | |
| 4,983,125 | A | 1/1991 | Smith et al. | |
| 5,215,468 | A | 6/1993 | Lauffer et al. | |
| 5,421,236 | A | 6/1995 | Sanger | |
| 5,511,982 | A | 4/1996 | Pigache et al. | |
| 5,529,498 | A | 6/1996 | Cassily et al. | |
| 5,743,744 | A | 4/1998 | Cassily et al. | |
| 5,888,074 | A | 3/1999 | Staplin et al. | |
| 5,898,421 | A | * 4/1999 | Quinn | 345/156 |
| 5,913,310 | A | 6/1999 | Brown | |
| 6,030,226 | A | * 2/2000 | Hersh | 434/236 |
| 6,113,538 | A | 9/2000 | Bowles et al. | |
| 6,186,145 | B1 | * 2/2001 | Brown | 600/300 |
| 6,200,138 | B1 | * 3/2001 | Ando et al. | 434/61 |

* cited by examiner

METHOD AND APPARATUS OF ENHANCING LEARNING CAPACITY

CROSS-REFERENCE TO RELATED APPLICATIONS

This application claims priority from International Patent Cooperation Treaty application Ser. No. PCT/US00/22160 filed on Aug. 11, 2000, which claims priority from provisional patent application Ser. No. 60/186,091 filed on Aug.13, 1999, and provisional patent application Ser. No. 60/219,321 filed on Aug. 13, 1999 and provisional Application 60/189,091 filed Mar. 14, 2000, the disclosures of which are incorporated herein in their entirety by reference.

BACKGROUND OF THE INVENTION

This invention relates generally to a method and apparatus for enhancing learning capacity. While the invention is useful with individuals of all ages, it provides a technique which does not necessarily involve overt surface behavior of the individual and, thereby, can be used by young children and infants.

In U.S. Pat. Nos. 5,529,498 and 5,743,744, the disclosures of which are hereby incorporated herein by reference, I disclose a neuro-motor coordinating measuring and enhancing apparatus and method. The technique described in my previous patents includes generating and, at least occasionally, presenting to the user repetitive occurrences of a reference signal, the occurrences being separated by a time interval, and receiving from the user with a trigger a response to the user's prediction of the lapse of the predetermined time interval since the last occurrence of the reference signal. The temporal relationship between the response of the user and the predetermined time interval since the last occurrence of the reference signal is determined and used to generate a guidance signal that is a function of the temporal relationship. The guidance signal draws the user into time alignment with occurrence of the reference signal.

In view of the outstanding success of using the techniques disclosed in my prior patents to improve neuro-motor functioning, I have also conceived of using such techniques as planning and sequence training to enhance the learning capacity of individuals. This conception has been evaluated utilizing a peer-reviewed research project as will be discussed in more detail below.

It is important that young children be provided with the exceptionally helpful capabilities of the rhythmicity training disclosed in my previous patents. As told in Kotulak, R., "Inside the Brain, Revolutionary Discoveries of How the Mind Works," Andrews McMeel Publishing, 1997, although the brain is capable of learning throughout life, nothing will ever match the activities that go on during the early days of a child. In the course of the first three years, a totally dependent child will build an incredibly complex new brain that will enable him or her to walk, talk, analyze, care, love, play, explore, and have a unique emotional personality.

Although the techniques disclosed in my patent are of immeasurable advantage to a user, I have discovered that further enhancements increase this advantage.

SUMMARY OF THE INVENTION

According to an aspect, the present invention provides a method of enhancing a user's learning capacity. The method includes generating a reference signal having occurrences separated by time intervals, providing a trigger and receiving a user's manipulation of the trigger. The method further includes determining a temporal relationship between user manipulation of the trigger and occurrences of the reference signal. The method further includes generating a guidance signal that is a function of the temporal relationship and at least occasionally presenting the guidance signal to the user.

An apparatus according to an aspect of the invention includes a user operable trigger that receives user manipulation of the trigger and a control. The control generates a reference signal having occurrences separated by time intervals. The control determines a temporal relationship between user manipulation of the trigger and occurrences of the reference signal. The control further at least occasionally provides a guidance signal to the user that is a function of the temporal relationship. The guidance signal is substantially withheld from the user for user manipulations of the trigger signal that are within a particular range. The particular range encompasses an occurrence of the reference signal. Preferably, the particular range extends on the order of 15 milliseconds before to 15 milliseconds after the reference signal.

An apparatus according to another aspect of the invention includes a user operable trigger which receives a user manipulation of the trigger. The apparatus further includes a control generating a reference signal having occurrences separated by a predetermined time interval and determining a temporal relationship between user manipulation of the trigger and occurrences of the reference signal. The control further generates a direction signal directing a user manipulation of the trigger. Preferably, the control causes the direction signal to selectively direct a user to manipulate the trigger either before the reference signal or after the reference signal.

According to a more specific aspect of the invention, the direction signal is supplied with a visual output and depicts motion in a particular direction; for example, a forward movement along a road or the like. The direction signal selectively directs a user to manipulate the trigger either before or after the reference signal as alternate lateral movement with respect to the depicted direction of motion. The direction signal may further indicate a user's response to the direction signal such as by varying rate of the motion in the particular direction.

According to another aspect of the invention, the control has an aural output supplied to a pair of stereo headphones having left and right speakers. The aural signal supplied by the control to the headphone speakers varies the spatial perception of the guidance signal within the brain of the user. The guidance signal is generated to vary its spatial perception by the user as a function of the temporal relationship between user manipulation of the trigger and occurrences of the reference signal.

An apparatus according to another aspect of the invention includes a trigger adapted to be manipulated by a young child user and an output which provides a signal to the user. The apparatus further includes a control that is responsive to a user manipulation of the trigger for generating a reference signal having occurrences separated by time intervals. The control further determines a temporal relationship between user manipulation of the trigger and occurrences of the reference signal. The control causes the output to at least occasionally provide a guidance signal to the user that is a function of the temporal relationship.

In one embodiment, the trigger includes a body having a handle adapted to be grasped by a young child, such as a pre-toddler child, or the like, and a motion sensor responds to movement of the body. An output, which may be aural, visual, or both, provides the guidance signal to the user. The motion sensor may include an accelerometer and the output may produce a reward signal in response to either rhythmic movement of the body by the child, rotational movement of the body by the child, or both. The body may further include an orientation member, such as a spinning mass gyroscope, or the like, which is operable by the control in order to dispose the body toward a particular orientation. This is useful in assisting the child in progressing from random motions to rhythmic periodic rotational movements which are non-ballistic in nature. In another embodiment, the trigger may be a member adapted to be suspended above a child's play area or sleep area and a sensor which responds to movement of the member.

These and other objects, advantages, and features of this invention will become apparent upon review of the following specification in conjunction with the drawings.

DESCRIPTION OF THE PREFERRED EMBODIMENT

Figure 1:
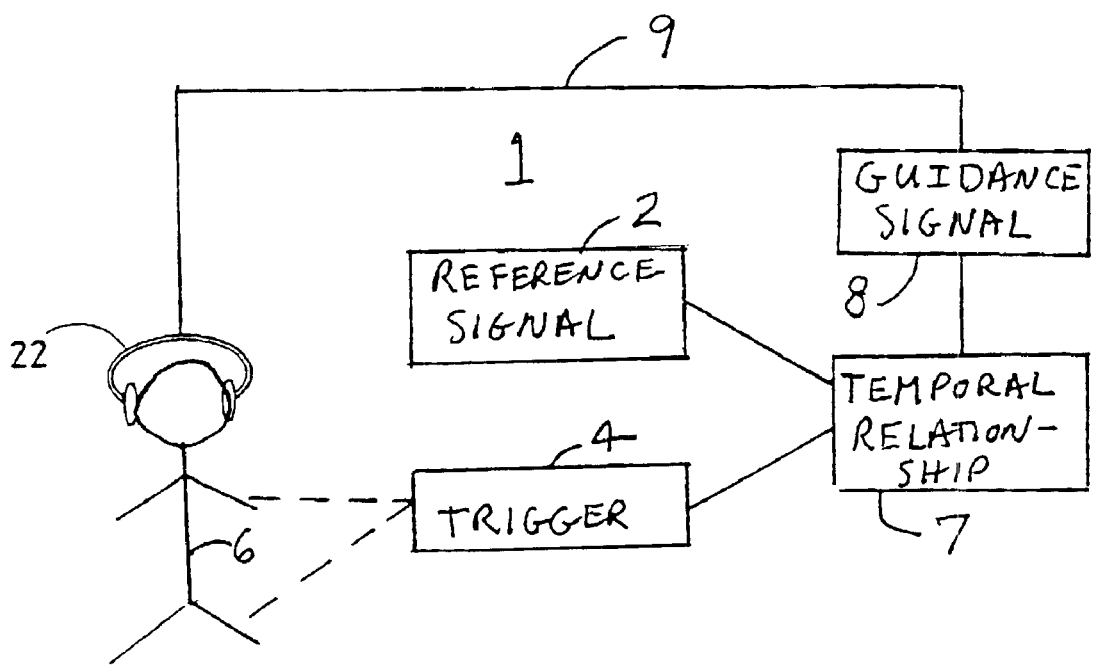
FIG. 1 is a diagram of a method of enhancing a user's learning capacity according to the invention.

Referring now specifically to the drawings, and the illustrative embodiments depicted therein, a method (1) of enhancing a user's learning capacity includes generating a reference signal (2) having occurrences separated by time intervals and providing (4) a trigger and receiving (6) a user's manipulation of the trigger. The method further includes determining (7) a temporal relationship between the user's manipulation of the trigger and occurrence of the reference signal and generating (8) a guidance signal that is a function of the temporal relationship. The guidance signal is at least occasionally presented (9) to the user.

A report entitled "Effect of Interactive Metronome® Training on Children With ADHD," authored by Dr. Robert J. Shaffer et al., and attached as Exhibit A hereto, was the result of 19 children receiving 15 hours of planning and sequence training exercises according to the principles of my prior patents compared with a comparison group receiving no intervention and a second control group receiving training on selected video games. The Shaffer et al. report found statistically significant differences among 12 factors on performance in areas of attention, motor control, language processing, reading, and parental reports of improvement in regulation of aggressive behavior.

Figure 2:
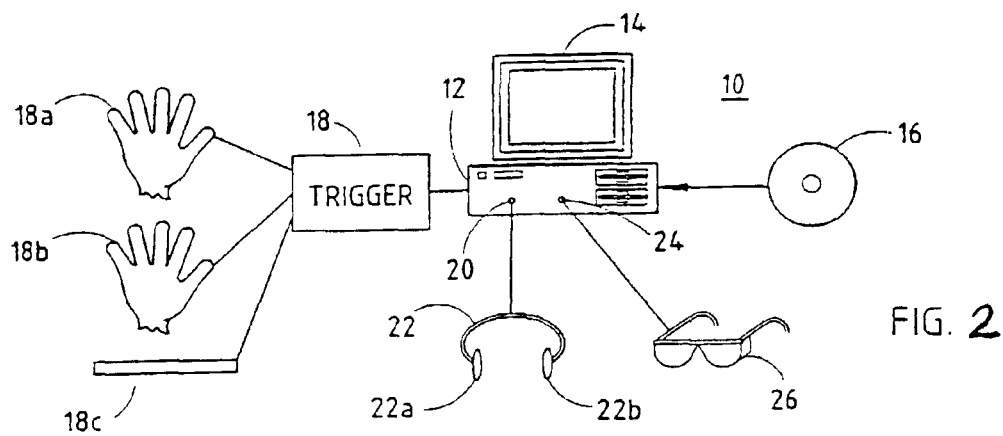
FIG. 2 is a block diagram of an apparatus according to the invention.

Method (1) of enhancing a user's learning capacity is preferably performed on a learning capacity enhancement apparatus 10, that is illustrated as including a computer CPU 12, a monitor 14, and a computer readable media 16 containing a program to be loaded on computer 12 in order to operate apparatus 12 (FIG. 2). Computer 12 is preferably an IBM, or compatible, computer with a 100 megahertz Pentium processor or higher having a Windows '98 or '95 operating system and 16 megabytes or more of RAM. An Apple-based platform may also be used. Computer 12 may be a personal computer (PC), a network computer, a handheld computer, such as the PalmPilot or Psion units, a Nintendo GameBoy unit, a Nintendo PlayStation unit, and a Sega DreamCast unit, or the like. Preferably, computer 12 has a hard drive memory device having at least 30 megabytes of available space. One or more triggers 18 are connected with a standard 9 pin connector serial port of computer 12. Computer 12 preferably has a stereo sound card (not shown) along with MIDI and WAV capability. Computer 12 has an aural output 20 which is connected with a pair of stereo headphones 22. Computer 12 may additionally have a video output 24 which is connectable with a virtual reality headset 26.

Figure 3A:
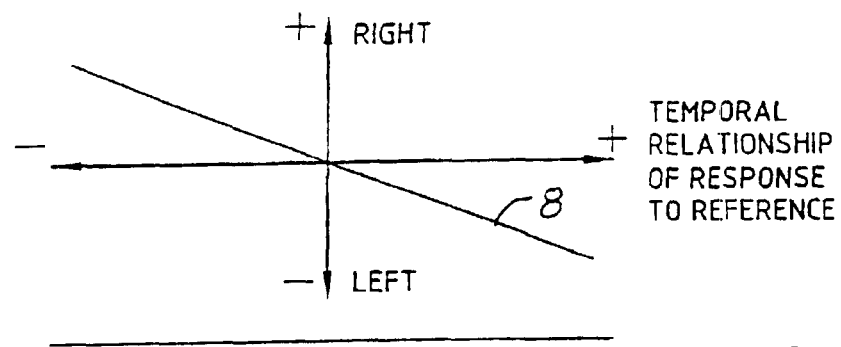
FIG. 3a is a diagram illustrating one form of an association between a guidance signal and the temporal relationship of actuation of the trigger to an occurrence of the reference signal.
Figure 3B:
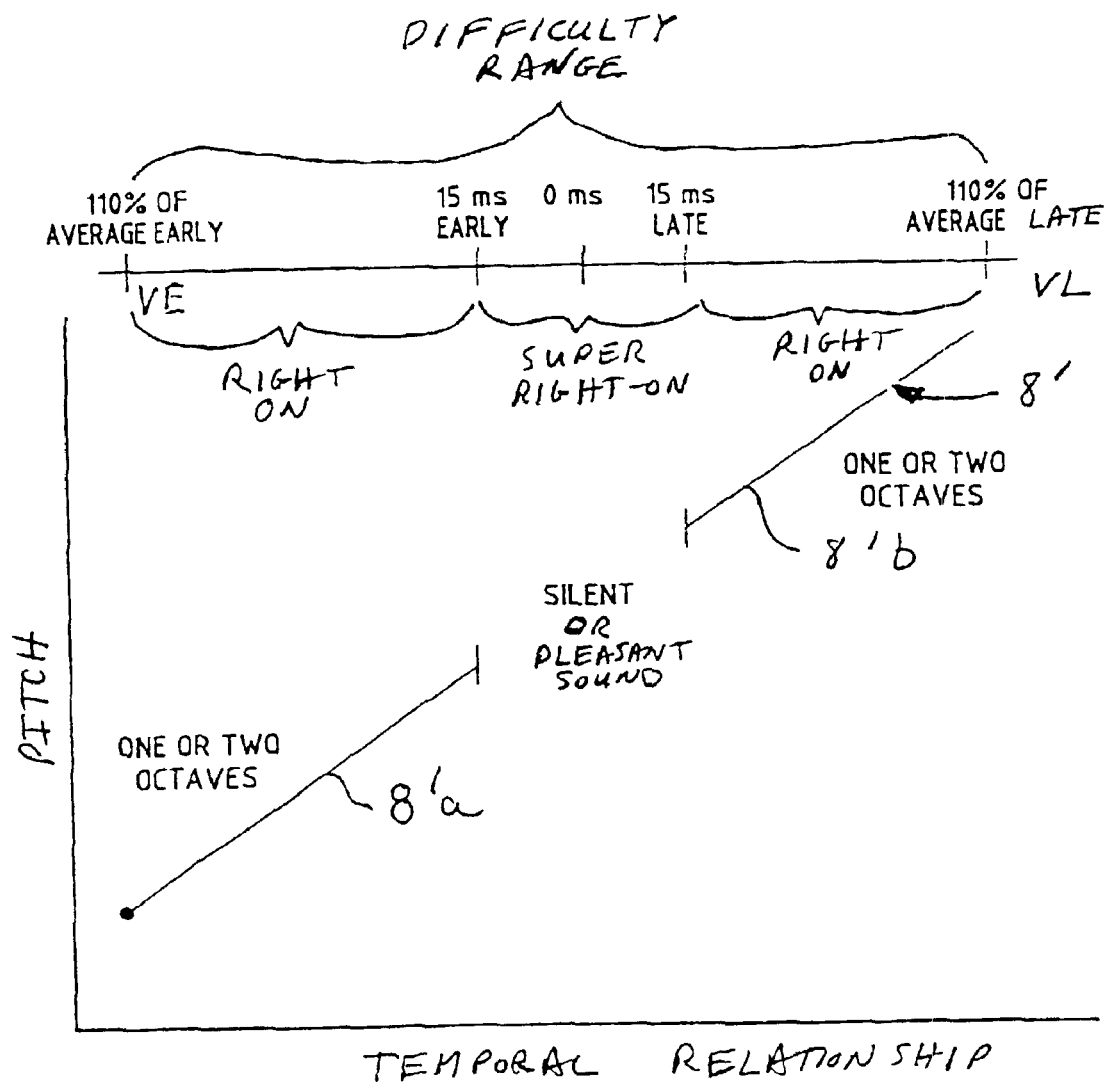
FIG. 3b is the same view as FIG. 3a illustrating another form of an association between a guidance signal and the temporal relationship of actuation of the trigger to an occurrence of the reference signal.

Aural output 20, in one embodiment of method 1, supplies signals to speakers 22a and 22b of stereo headphones 22 in a manner that varies the guidance signal, or guide tone, from left speaker 22a to right speaker 22b in order to vary the perceived spatial location of the guidance signal within the head of the user by using conventional stereo signal mixing techniques. This can be illustrated in FIG. 3a in which the guide tone 8 is seen drifting spatially toward the right side of the user's head for responses that are before the reference and drifting towards the left side of the user's head for responses that are after the reference, or vice versa. The variation of the guide tone from left-to-right speakers of headphone 22 may be done in combination with variation of the frequency of the guide tone or other techniques. As illustrated in FIG. 3b, guidance signal 8' is provided in a difficulty range that includes a portion 8'a that is generated for user activation of trigger 18 during a "right-on" range before reference signal 2 and a portion 8'b that is generated for user manipulation of trigger 18 during a "right-on" range after the occurrence of reference signal 2. A particular range, referred to as a "super right-on" range, is established in a manner that encompasses an occurrence of reference signal 2 and indicates an exceptionally accurate manipulation of the trigger. In the illustrated embodiment, difficult range DR extends from 15 milliseconds prior to the reference signal to 15 milliseconds after the reference signal, although a greater or lesser value may be selected. Difficulty range DR is established in order to identify a manipulation of trigger 18 by the user. When user manipulation of trigger 18 falls within the "super right-on" range, the guidance signal 8, 8' is withheld as a reward to the user. The user may be provided with no sound besides the reference signal for "super right-on" responses. Alternatively, the user may be provided with a pleasing sound for "super right-on" responses. An example of a pleasing sound would be one that is not percussive. Another example of a pleasing sound is one having a relatively low volume.

For responses that are in the "right-on" range earlier than the reference signal, guidance signal 8'*a* varies in pitch according to the amount that the user response is early with respect to the reference signal 2. In the illustrated embodiment, guidance signal portion 8'*a* extends over one or two octaves, but a greater or lesser scale may be used. For responses that are in the "right-on" range that occur late with respect to the reference signal, guidance signal portion 8'*b* is at a higher pitch than guidance signal portion 8'*a* and, preferably, extends over one or two octaves, but may be greater or lesser than this amount. In the illustrative embodiment, a linear relationship exists between guidance signal portions 8'*a* and 8'*b* on opposite sides of the reference signal. The purpose of guide sounds 8, 8'*a* and 8'*b* is to naturally and subconsciously draw the user toward the reference signal.

For responses prior to difficulty range DR, referred to as point VE, a sound may be produced that is distinctive from guidance signal 8' such as a human voice sound. Preferably, the human voice says "oops" in a low tone for very early responses. Similarly, a user response that is very late (VL) may result in a sound that is noticeably different from that produced by guidance signal 8'. An example is a human voice saying "oops" in a high tone, or vice versa. Other distinctive sounds may be used outside of the difficulty range, such as a musical sound that differs from guide tone 8', an annoying sound, or the like.

In the illustrative embodiment, the locations of very early (VE) and very late (VL) sounds are adaptively established at a percentage of the average early and late, respective, responses by the user. In the illustrative embodiment, a very early point is established at 110 percent of average early user manipulations of the trigger and a very late (VL) point is established at 110 percent of average late manipulations of the trigger by the user, although a different percentage may be selected. The purpose of making the difficulty range adaptive to the user is to keep the task easy enough to motivate the user and difficult enough to keep the user challenged and learning enhancement progressing. Whenever a user is capable of producing multiple such "right-ons" in a row, then a multiple burst performance is observed. A goal may be set, for example, to obtain a certain number of multiple bursts per 1,000 repetitions with apparatus 10.

Upon initial setup, the software on media 16, when loaded in CPU 12, performs a test on the timecard included with computer 12 in order to verify its accuracy in time reproduction. If the timecard operates satisfactorily, then the software on media 16 may utilize the timecard to generate the signals supplied to headphone 22. Otherwise, the software on media 16 will generate tones supplied to headphone 22 utilizing MIDI and WAV files, or the like, included with the operating system for computer 12 as would be apparent to those skilled in the art.

Trigger 18 may include a hand trigger 18*a*, a hand trigger 18*b*, and a foot trigger bar 18*c* in order to allow the user to respond to a series of exercises involving one or more of the triggers 18. This may include, by way of example, clapping both hands together, clapping both hands together with guide sounds, tapping preferred hand, tapping non-preferred hand, alternating toe taps, tapping the preferred toe, tapping the non-preferred toe, alternating heel taps, tapping with the preferred heel, tapping with the non-preferred heel, alternating preferred hand/non-preferred toe taps, alternating non-preferred hand/preferred toe taps, balancing on the preferred foot and tapping with the non-preferred toe, balancing on the non-preferred foot and tapping with the preferred toe, and the like. Other exercises will suggest themselves to the skilled artisan. Additionally, the trigger may be attached to another item that the user directly manipulates, such as a golf club, or the like. As the user performs the various exercises with triggers 18, a reference signal and a guide signal are normally supplied through headphones 22. However, the reference signal may occasionally be eliminated in order to allow the user to operate from the guidance signal alone. It should be understood that other forms of guidance signals are possible, including visual guidance signals, as will be discussed in more detail below. Alternatingly, the guidance signal may be omitted entirely during certain routines, such as those used to measure a user's response to planning and sequencing training.

Apparatus 10 may include an additional tool to further improve the timing accuracy of the user. Apparatus 10 produces a direction signal 27 which is displayed on a visual display, such as monitor 14, virtual reality headset 26, or the like. The purpose of the direction signal is to direct the user to manipulate trigger 18 in a fashion that is altered from the usual procedure of attempting to manipulate the trigger as close to the anticipated occurrence of the reference signal as possible. One way to direct the user to alter the operation of the trigger is to direct the user to produce a series of responses which are intentionally before the occurrence of the reference signal. Another direction to provide the user is to produce a series of responses that are intentionally after the occurrence of the reference signal. By providing the user not only the tools for producing a series of responses that are close to the reference signal, but also a series of responses that are intentionally before the reference signal and a series of responses intentionally after the reference signal, the user achieves an enhanced sense of timing accuracy. Direction signal 27 may be applied once the user becomes capable of producing a number of multiple "super right-on" bursts within a given number of repetitions, such as 80 to 90 multiple bursts for 1,000 repetitions. Additionally, a distraction signal may be provided to the user, along with the reference signal in order to assist the user in mentally filtering out external distractions and focusing subconsciously on the reference signal.

Figure 4:
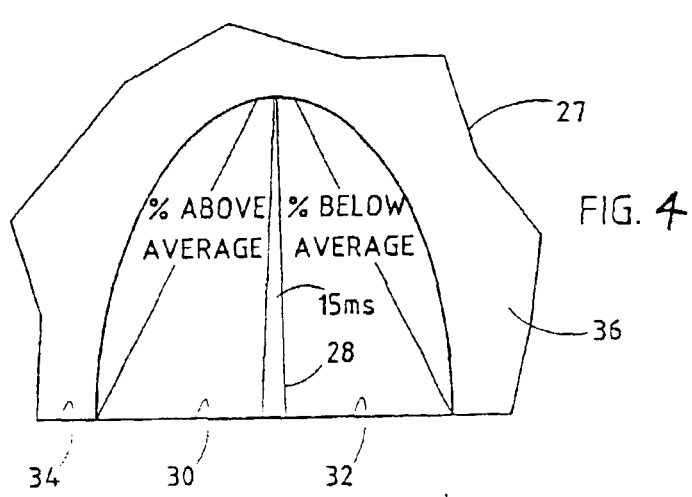
FIG. 4 is a side view of a visual display generated by the apparatus in FIG. 2.

A "virtual tunnel" including a direction signal 27 is illustrated in FIG. 4 in which geometric shape 28, such as a stripe down the middle of a virtual road, represents a particular accuracy level of user response, such as a "super right-on" response of 15 milliseconds or less, an adaptive "right-on" or "difficulty range," or another such value. Stripe 28 is surrounded to the left with a zone 30 representing a portion of an adaptive range representing a before-the-beat response and a zone 32 representing a portion of an adaptive range representing an after-the-beat response. The direction signal 27 also includes out of bound zones 34 and 36. Zone 34 indicates a VE response by the user that is too far ahead of the reference to be within the adaptive range 30. Zone 36 indicates a VL response by the user that is too far behind the reference to be within the adaptive range 32. Preferably, adaptive zones 30 and 32 are adaptive ranges which widen or narrow in response to worsening or improvement in the user's response. When a user response falls within either zone 34 or 36, a distinctive sound may be generated. The distinctive sound may be a human voice saying something such as "oops," an annoying negative response generated in the headphone, such as a "buzzer," "bong," or the like. Direction signal 27 is preferably generated by computer 12 in a manner which gives a sense of movement along stripe 28. This sense of movement can be caused by changes in the geometry of the tunnel, features on the tunnel walls, such as rocks or bricks, breaking stripe 28 into a series of segments that appear to be moving, or the like, as would be well within the capability of the skilled artisan. As the user generates responses in zone 28, the user will appear to move along the scene defined by direction signal 27 at a particular rate which may initially be an increasing rate. If, however, the user response causes the user to hit a "wall" in zone 34 and 36 more than a particular number of times in a row, such as two or three times, this action causes the motion along stripe 28 to slow down or stop. Thus, when a user is able to respond consistently in zone 28, the user receives a sense of motion and, when the user hits a "wall" 34, 36, the user receives a sense of being held back. This causes the user to realize that their response is off of the reference in order to pull the user into synchronism with the reference.

Figure 5:
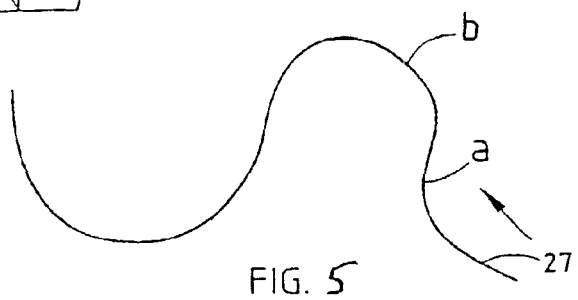
FIG. 5 is a top view of the display generated in FIG. 4.

As viewed in FIG. 5, the virtual "tunnel" scene in FIG. 4 bends to the right and left as the user moves along stripe 28. The relationship between the reference signal, user response and guidance signal remains constant relative to the virtual space occupied by geometric space 28. As the tunnel scene bends to the right, as at point A (FIG. 5), the user is forced to produce responses in zone 32, which is after the reference, in order to avoid hitting a wall. When the tunnel scene bends to the left, as at point B (FIG. 5), the user is forced to give responses in zone 30, which is before the reference, in order to avoid hitting a wall. Other "virtual" landscapes can be used, such as attempting to rise a balloon over a mountain, or the like, to produce a direction signal. It can be seen that direction signal 27 provides a useful timing exercise which enhances not only the user's sense of interactivity with the reference, but also requires the user to be able to selectively and controllably move the user's responses prior to the occurrence of the reference signal and after occurrence of the reference signal. It has been found that this further extends the planning and sequence training which enhances learning capacity in areas such as user attention, language processing, reading skills, and regulation of aggressive behavior.

Figure 6:
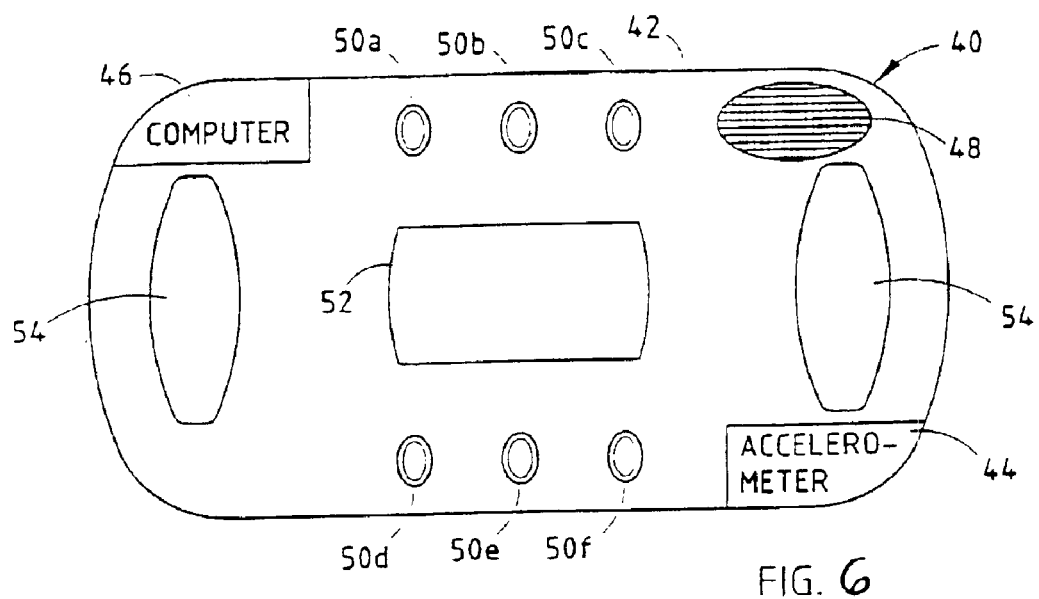
FIG. 6 is a side elevation of an alternative embodiment of the apparatus in FIG. 2.
Figure 7:
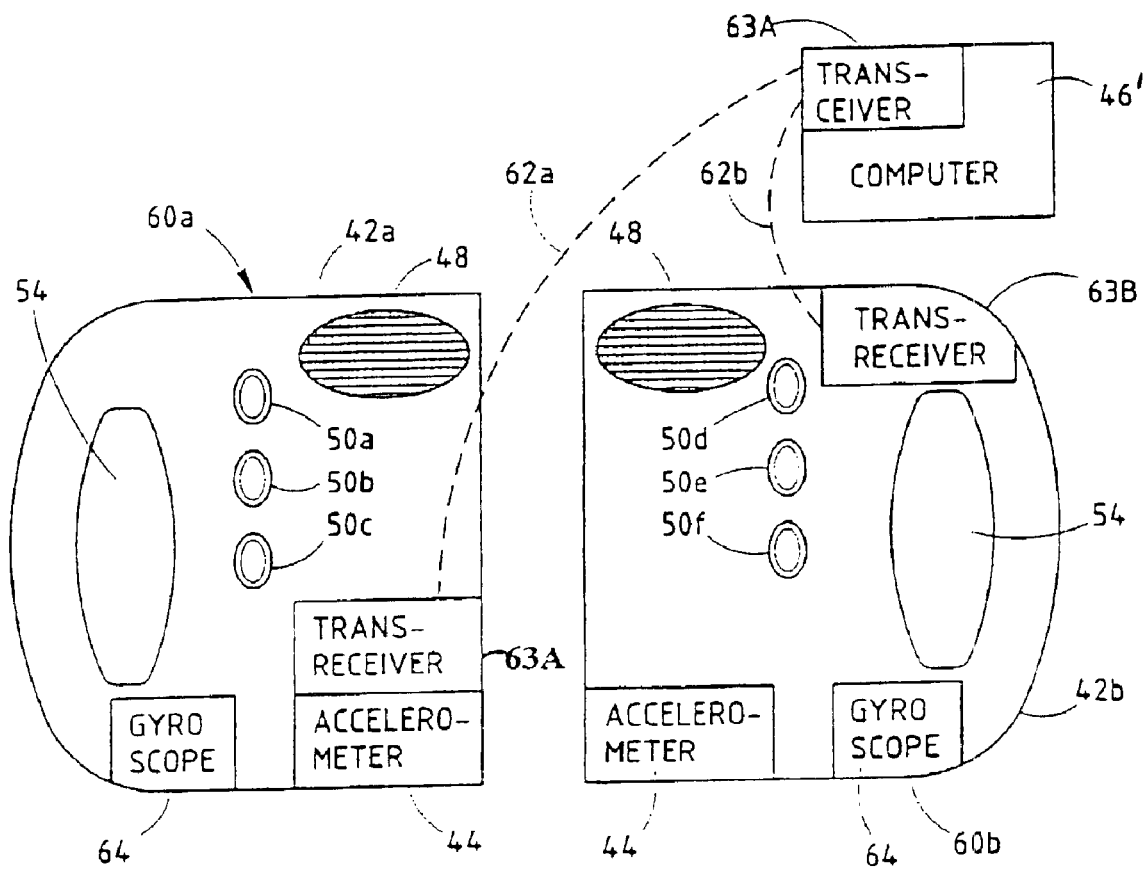
FIG. 7 is the same view as FIG. 6 of an alternative embodiment thereof.

A learning capacity enhancement apparatus 40, which is adapted to be operated by a young child, such as an infant, a pre-toddler, a toddler, or the like, includes a trigger that is adapted to be manipulated by a young child user (FIG. 6). In one embodiment, the young child manipulatable trigger includes a body 42 with one or more handle portions 54. A motion sensor 44 moving with the body and a computer 46 monitor manipulation of body 42 by the user. One or more outputs are provided to at least occasionally provide a guidance signal to the user, such output may include a speaker 48, in order to produce aural outputs, a series of lights, preferably colored lights 50a–50f in order to produce various patterns of visual effects, and, optionally, a video display 52 (FIGS. 6 and 7). Motion sensor 44 may be an accelerometer, a motion-sensing circuit, a solid-state multi-axis accelerometer, or the like, which senses movement of body 42 by a user grasping a handle portion 54 of body 42. When initially grasped by the infant, apparatus 40 may produce a series of pleasant light displays on indicators 50a–50f and/or sounds on speaker 48 upon even random movement of the housing 42. As the infant begins to further move apparatus 40, additional rewards may be provided to the infant as the housing is moved in a constructive pattern, such as in a rhythmic, non-ballistic, pattern, such as a rotational movement in a particular plane. As the user generates such constructive patterns, a reference signal may subsequently be generated and supplied, such as with speaker 48, to the infant. The reference tone may be generated from an average of previous motions of the user. Alternatively, the reference tone may be generated internally by computer 46 and supplied to the young child or infant. As the user begins to move apparatus 40 in some timing that is close to the reference tones, the speaker 48 and/or visual indicators 50a–50f and 52 may provide guidance tones and/or reward indications to the user. After awhile, the user will be able to move apparatus 40 in a manner to produce regular pleasurable guide tones from speaker 48 and/or visual indicators 50a–50f and 52. It may also be desirable to produce instructive displays on display 52 with the audio portion coming from speaker 48. For example, the user can be "talked to" by a real or animated character in order to instruct the user as appropriate during the "training" sessions.

An alternative learning capacity enhancement apparatus 60a and 60b are individual units intended to be each grasped by a separate hand of the child (FIG. 7). Each unit includes a single handle portion 54, a speaker 48, and an accelerometer 44. In the illustrated embodiment, a control 46' is located remotely from apparatus 60a, 60b with a communication link 62a, 62b between each apparatus 60a, 60b and remote controller 46'. The communication links 62a, 62b are between a transceiver 61 associated with control 46' and separate transceivers 63a in apparatus 60a and 63b in apparatus 60b. This allows controller 46' to coordinate the responses to both apparatus 60a, 60b and to respond to the movements of both as a combination as would be apparent to the skilled artisan. Communication links 62a, 62b are preferably wireless and may be infrared links, may be radio frequency links, such as using the Bluetooth protocol, or the like. Each apparatus 60a, 60b may additionally include an orienting device 64, such as a spinning mass gyroscope, an electric motor, or the like. Each orientation device 64 is under the control of computer 46' and allows computer 46' to dispose the bodies 42a, 42b of each apparatus 60a, 60b in a particular orientation. This, for example, allows computer 46' to orient each apparatus body 42a, 42b in the same orientation that the body had during a previous exercise by the user. Also, the ability of computer 46' to affect the orientation of bodies 42a, 42b allows the computer to train the user in moving the body in a desirable rotational, non-ballistic, motion in a plane, while giving rewards to the user when the constructive movement is given. After the user obtains rewards with the help of orientation devices 64, then, eventually, computer 46 may discontinue use thereof.

Figure 8:
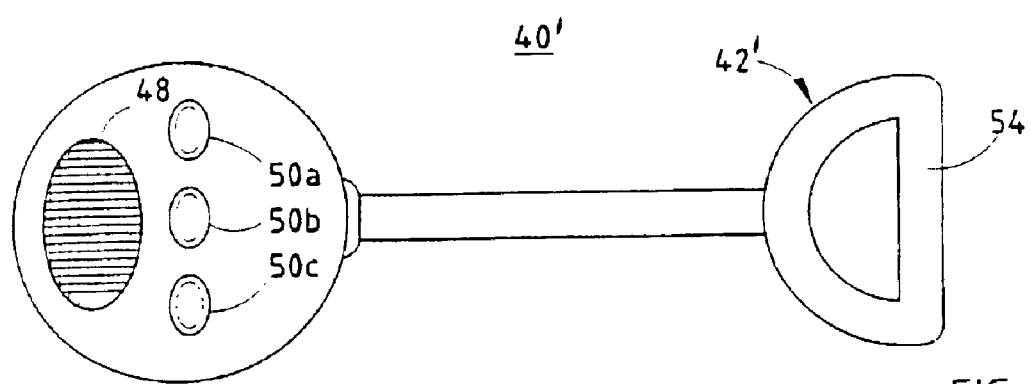
FIG. 8 is the same view as FIG. 6 of another alternative embodiment thereof.
Figure 9:
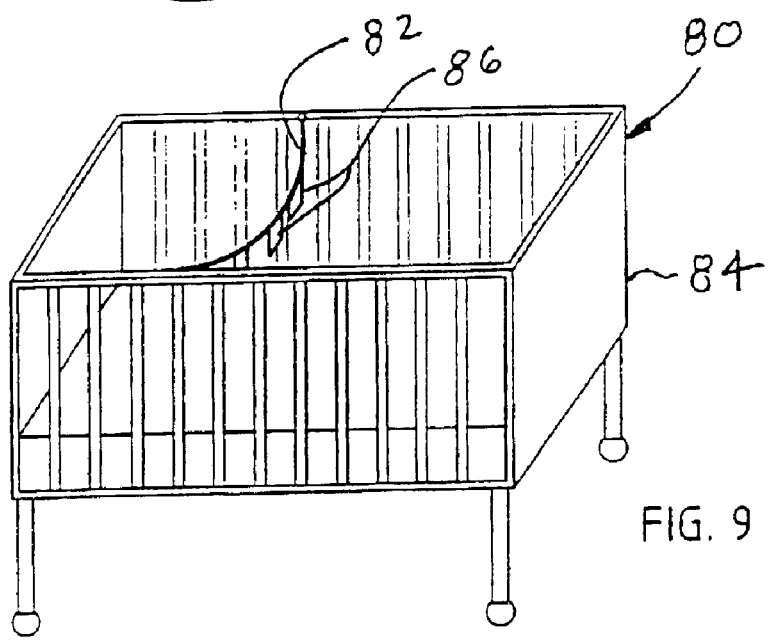
FIG. 9 is a perspective view of another alternative embodiment of the apparatus in FIG. 2.

Another alternative learning capacity enhancement apparatus 40' includes a housing 42' formed in the shape of a baby rattle having a handle 54' (FIG. 8). Otherwise, apparatus 40' is the same as apparatus 40, 60a, and 60b. Yet, an additional alternative learning capacity enhancement apparatus 80 includes a trigger assembly 82 which is adapted to be suspended above a playpen, crib, or the like, 84. Trigger 82 responds to contact by the child, such as by hitting or kicking a series of members 86 mutually supported above the crib or playpen 84. Preferably, members 86 are primary colors and may be in the form of various shapes, such as geometric shapes, animal shapes, or the like. External speakers (not shown) or flashing lights (not shown) may be activated in response to the child kicking or tapping elements 86. As the user strikes elements 86 in any form of a pattern, the activation of the speakers and/or flashing lights may increase in intensity, repetition, or the like. The purpose is to induce the user to continually improve the user's ability to operate in a rhythmic fashion as the user manipulates elements 86 of trigger 82. The purpose of the increased intensity and/or frequency of the responses is in order to keep the attention of the child and systematically motivate them to do better.

Figure 11:
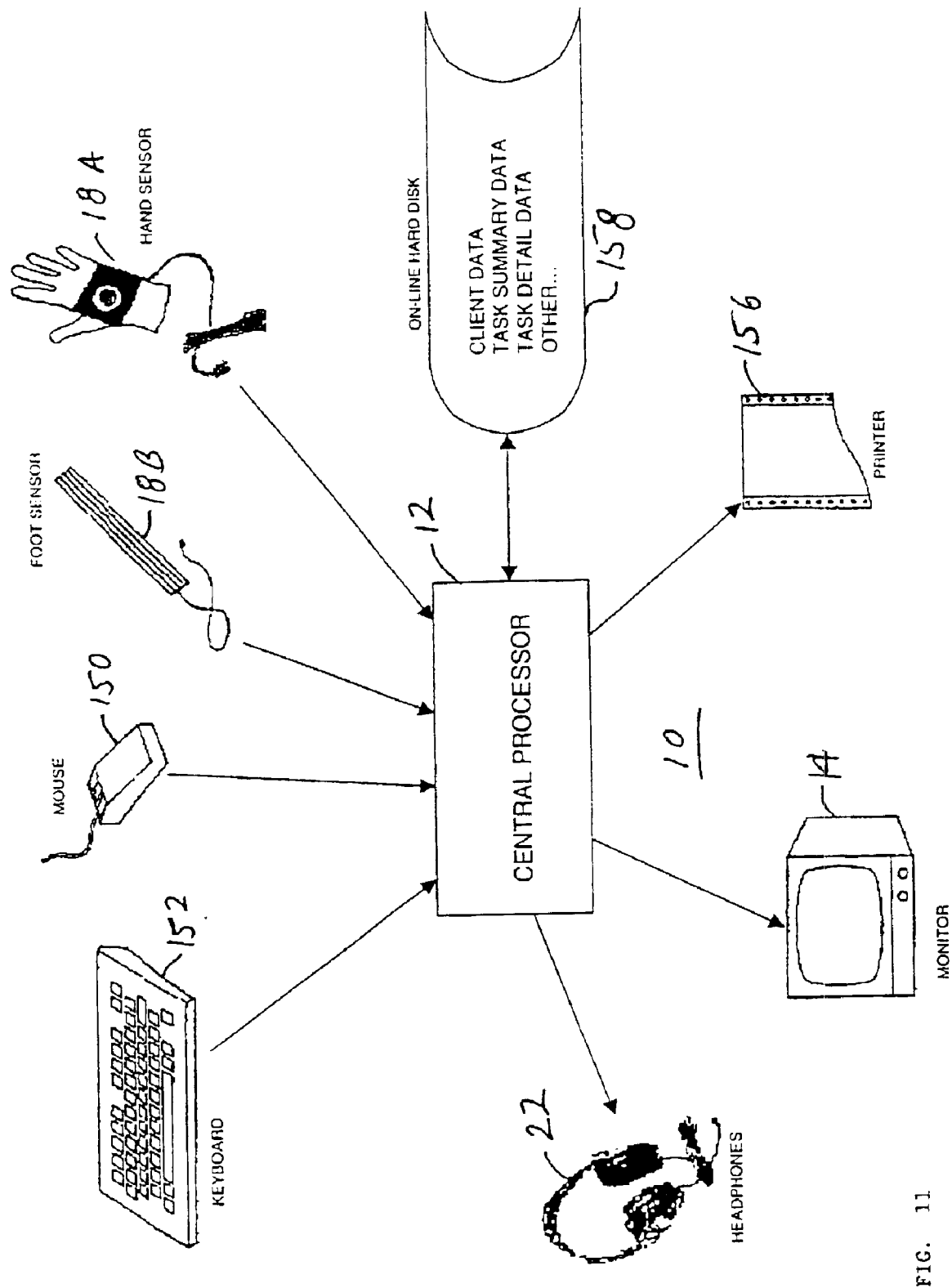
FIG. 11 is a somewhat more detailed view of the apparatus in FIG. 2.

A more detailed illustration of learning capacity enhancement apparatus 10 is illustrated in FIG. 11. In addition to a processor 12 and monitor 14, computer system 20 includes a mouse 150, keyboard 152, and printer 156. A hard drive 158 may contain information, such as client data, task summary data, task detail data, and other data.

Figure 12:
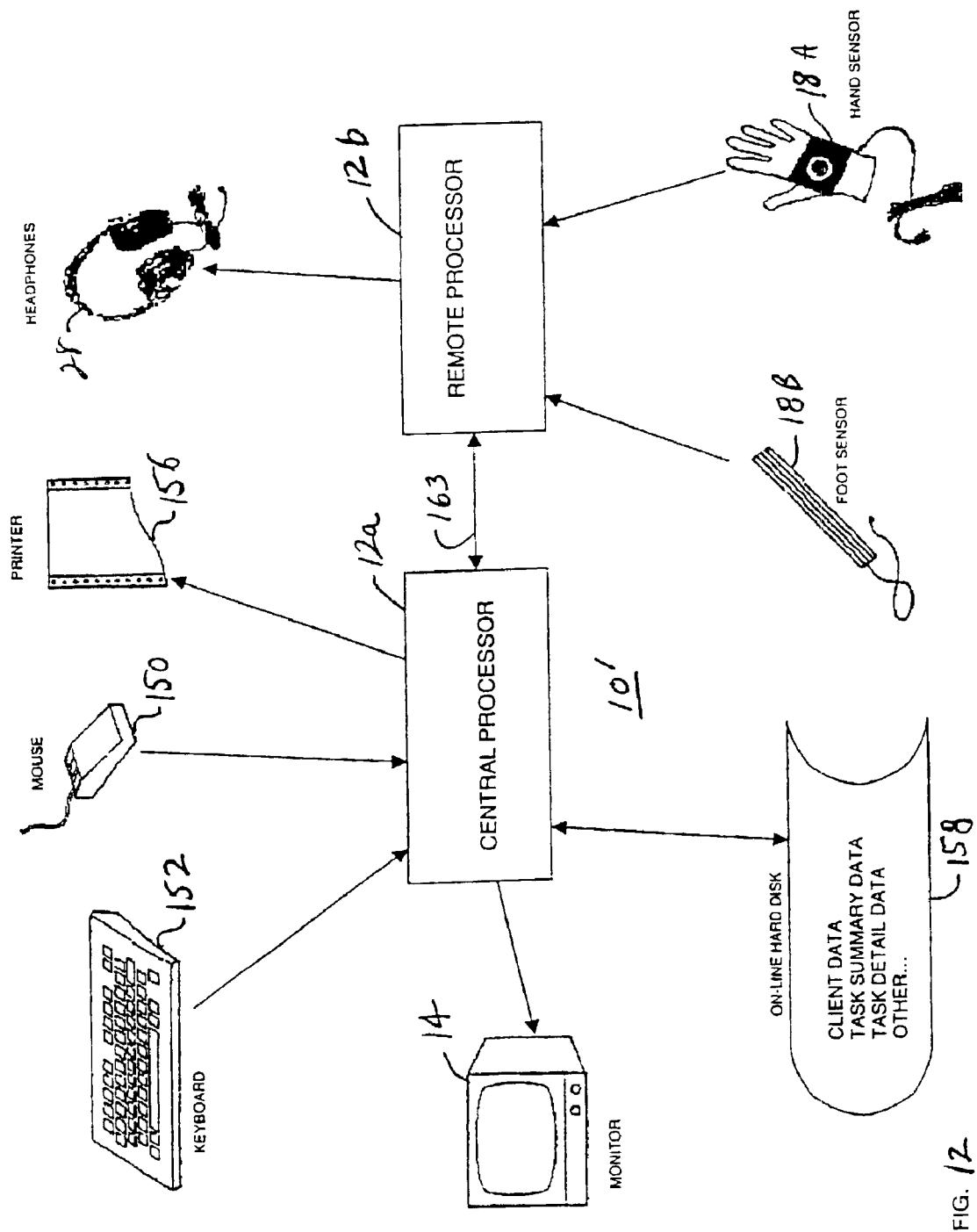
FIG. 12 is the same view as FIG. 11 of an alternative embodiment.

An alternative learning capacity enhancement apparatus 10' includes a central processor 12a and a remote processor 12b (FIG. 12). The central processor 12a may be dedicated to program administration, task management, data management, time sequence generation, and the like. Remote processor 12b may manage the input and output functions for the triggers 18a, 18b and user interface headphones 22. Remote processor 12b may also be responsible for generating the reference signals, distraction signals, guidance signals, and the like, provided to the user. Central and remote processors 12a, 12b may be joined by a communication link 163 which may be hard-wired, a local area network, a wide area network, or a global network, such as the Internet, or the like.

Figure 13:
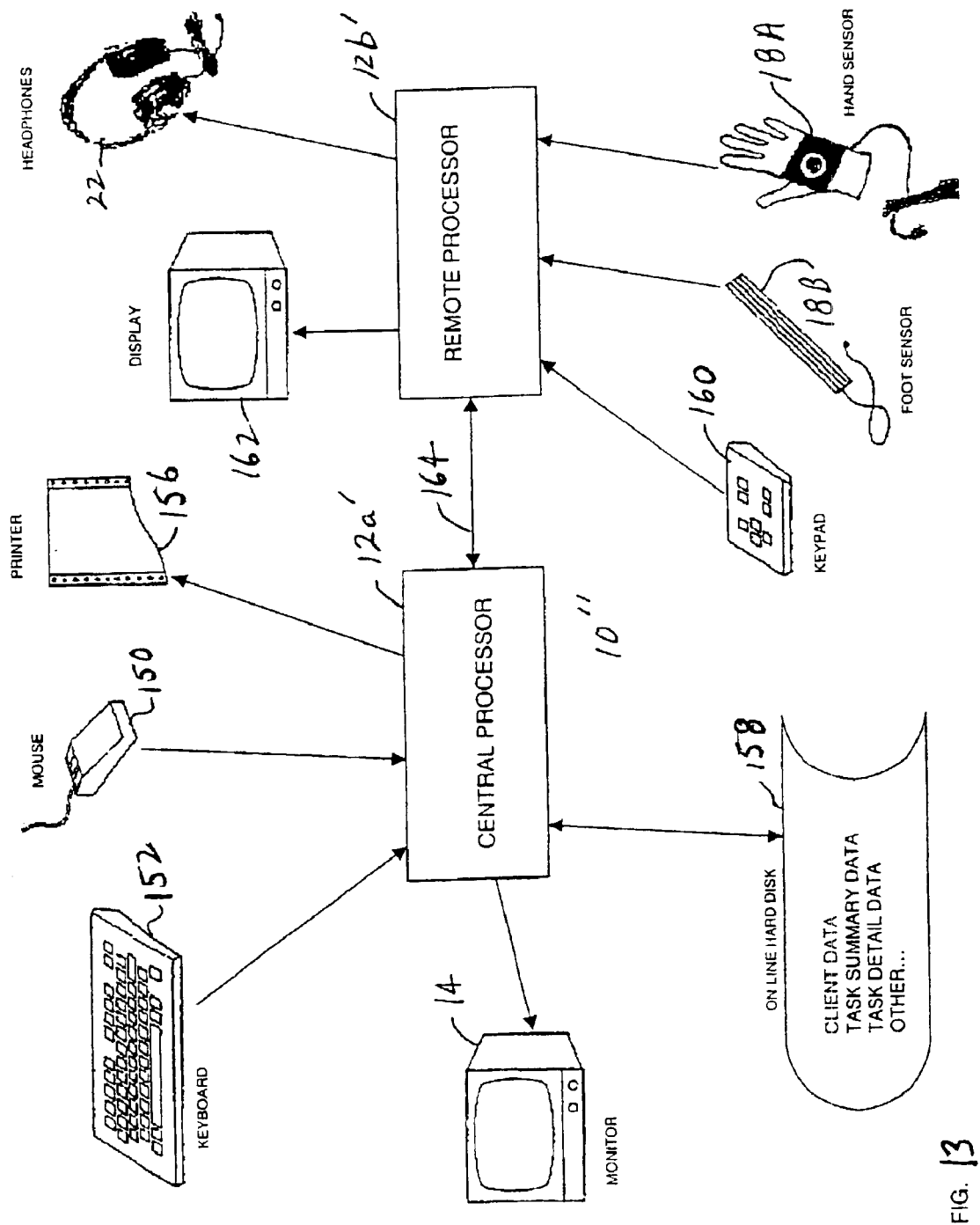
FIG. 13 is the same view as FIG. 11 of another alternative embodiment.

In another alternative embodiment, a learning capacity enhancement apparatus 10" includes a central processor 12a' and a remote processor 12b' (FIG. 13). In addition to handling the input/output for triggers and headphones, remote processor 12b' may include a keypad 160 and display 162. In this manner, remote processor 12b', keypad 160, and display 162 may be combined into a compact, portable device capable of being carried by the user, such as being attached to the user's belt, or the like, while the user wears headphones 22 and operates the triggers 18a and/or 18b. Remote processor 12b' may be connectable with central processor 12a' through a communication link 164 which may be a remote link, such as an infrared link, a radio frequency link, such as the Bluetooth protocol, or other known remote link. Central processor 12a' may be utilized to make changes to remote processor 12b' software and to process data generated at remote processor 12b'. Otherwise, remote processor 12b' may be operable in a standalone fashion.

Figure 14:
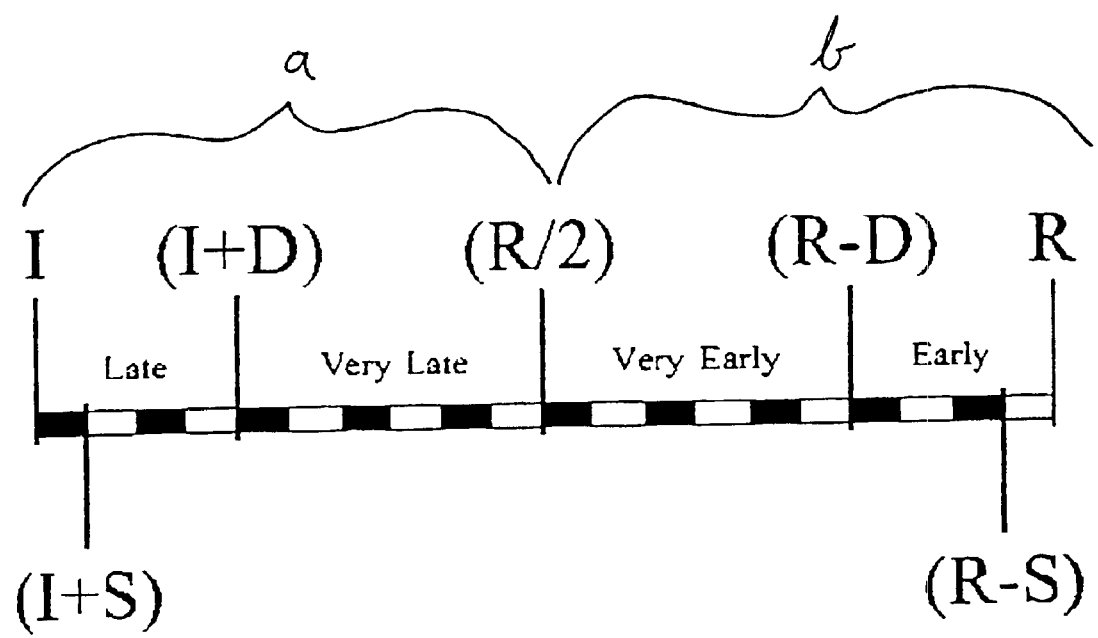
FIG. 14 is a diagram illustrating timing sequences of user manipulation of a trigger, or a response, with respect to occurrences of the reference signal.

An illustration of timing assessment carried out by learning capacity enhancement apparatus 12 is illustrated in FIG. 14. Referring to FIG. 14, the parameter I refers to the time that a reference signal is generated. The parameter R is an indication of the time at which another reference signal is generated. If a user's response occurs during interval "a," the response is late with respect to the reference signal occurring at I. If the user's response occurs during interval "b," the response is early with respect to the reference signal at R. The time intervals illustrated in FIG. 14 would be repeated for each sequence between occurrences of reference signals.

If the user responds in the period of I+S with respect to reference signal I, or in the period R–S with respect to reference signal R, the user response is deemed to be within the super difficulty range. This is considered a very accurate response. This may also be referred to as the "super right-on" range. If the user responds within the period of I+D, then the response is late with respect to reference signal I but within a difficulty range D. If a user responds within the range R–D, the response is deemed early with respect to reference signal R within the difficulty range D. If the user responds in the interval between I+D and R/2, the user response is deemed very late with respect to reference signal I. If the user response is in the range of R/2 to R–D, the response is deemed very early with respect to reference signal R.

Figure 15:
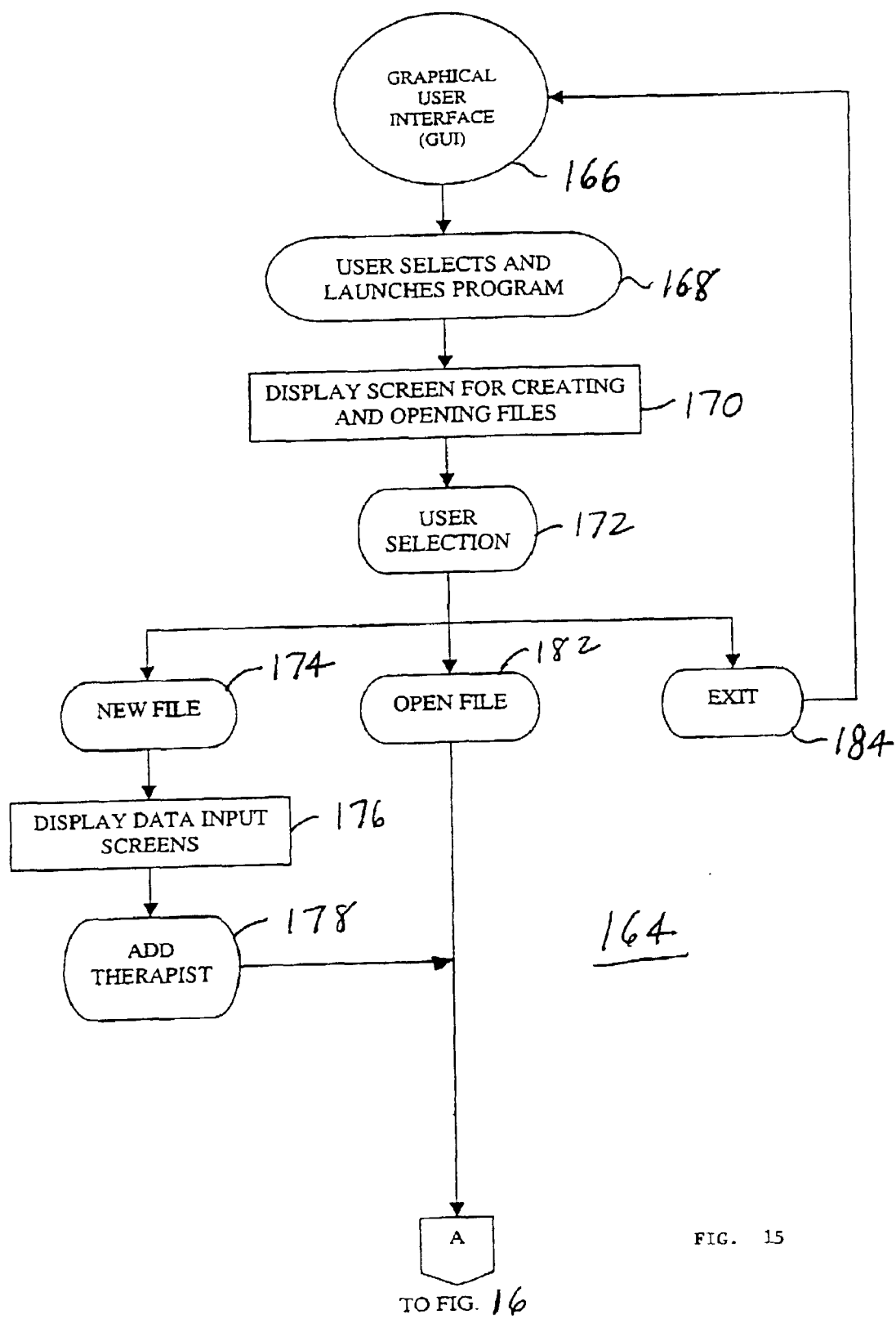
FIG. 15 is a flowchart of a data creation and input function.

A program 164 carried out by learning capacity enhancement apparatus 10 begins with a data creation and input function including a graphical user interface 166 displayed on monitor 14 from which the user selects and launches a program at 168 (FIG. 15). A screen, or menu, for creating and opening files is displayed on monitor 14 at 170 and the user is prompted to select a function to perform at 172. If the user selects a new file at 174, the monitor displays data input screens at 176. The program then provides for identifying the therapist at 178. If the user selects at 172 to open an existing file at 182, the file is opened and the screen for choosing a mode is displayed at 180. If the user selects to exit the program at 172, the program is exited at 184 and returned to the graphic user interface at 166.

Figure 16:
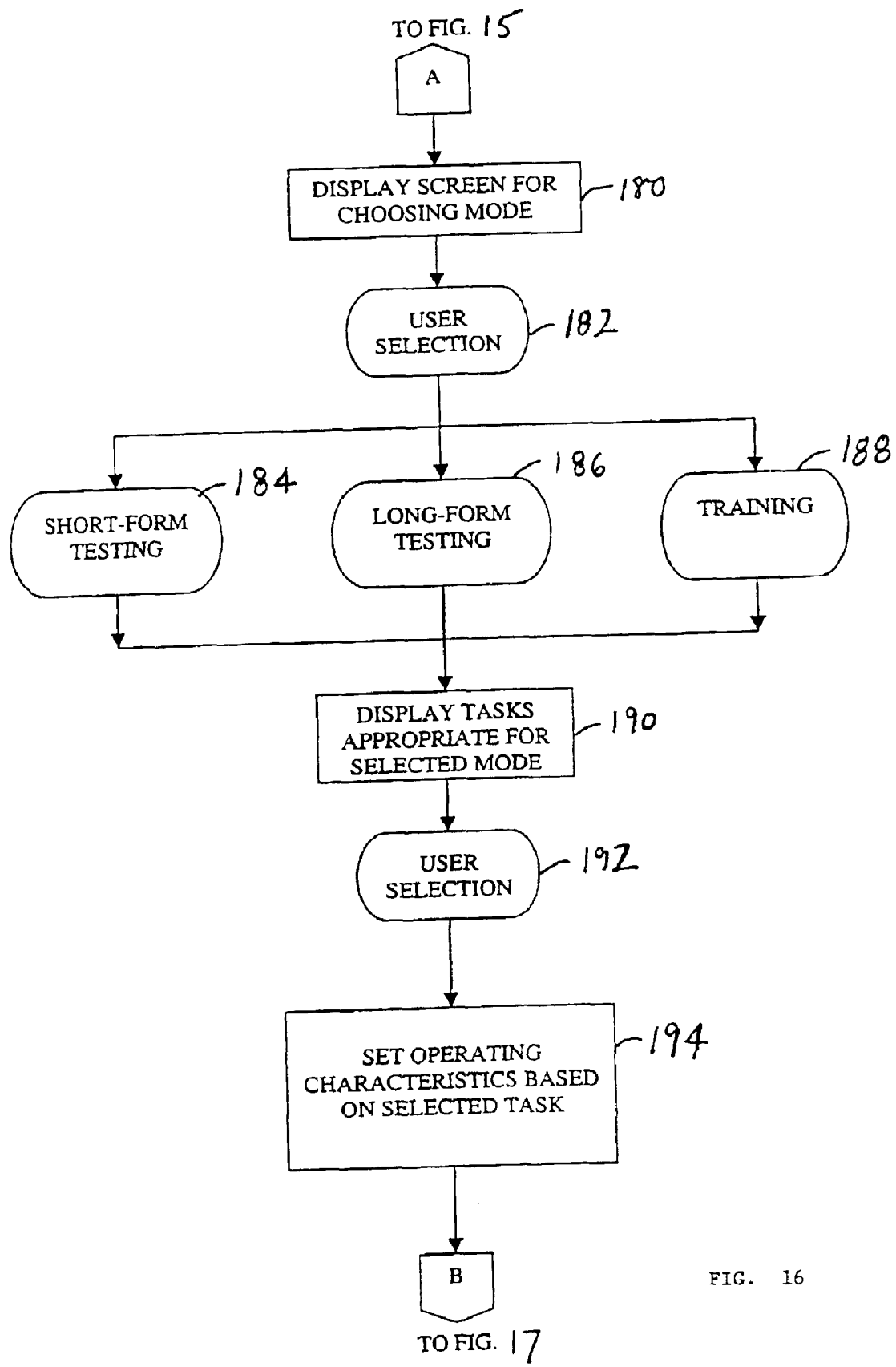
FIG. 16 is a flowchart of a mode and task selection function.

The program then proceeds to a mode and task selection function in which a screen is displayed at 180 for choosing a mode (FIG. 16). When the screen is displayed for choosing a mode at 180, the user makes a selection 182 from among a short-form testing routine 184, a long-form testing routine 186, and a training routine 188. The short-form testing mode 184 is a quick diagnostic tool with lower test/retest accuracy than the long-form test mode. Short-form test mode 184 includes a subset of the tests performed in the long-form testing mode, such as both hands clapping without guide sounds and/or both hands clapping with guide sounds. The short form is used primarily with users who are undergoing rhythmicity training 188 at the beginning and/or end of each session. The long-form testing mode 186 involves up to 14 or 16 tasks which are usually performed with no guide sounds being supplied to the user. The long form mode is primarily used when no rhythmicity training 188 is contemplated or prior to or after rhythmicity training. If the training mode 188 is selected, the user is presented with both reference sounds and guidance signals, or guidance signals alone, while the user is instructed to carry out various manipulations of hand sensor 18a and/or foot sensor 18b preferably under the guidance of a trained instructor or therapist. After the mode is selected at 182, the appropriate tasks are displayed on monitor 14 at 190 and operating characteristics may be selected by the user at 192 based upon the selected task at 194.

Figure 17:
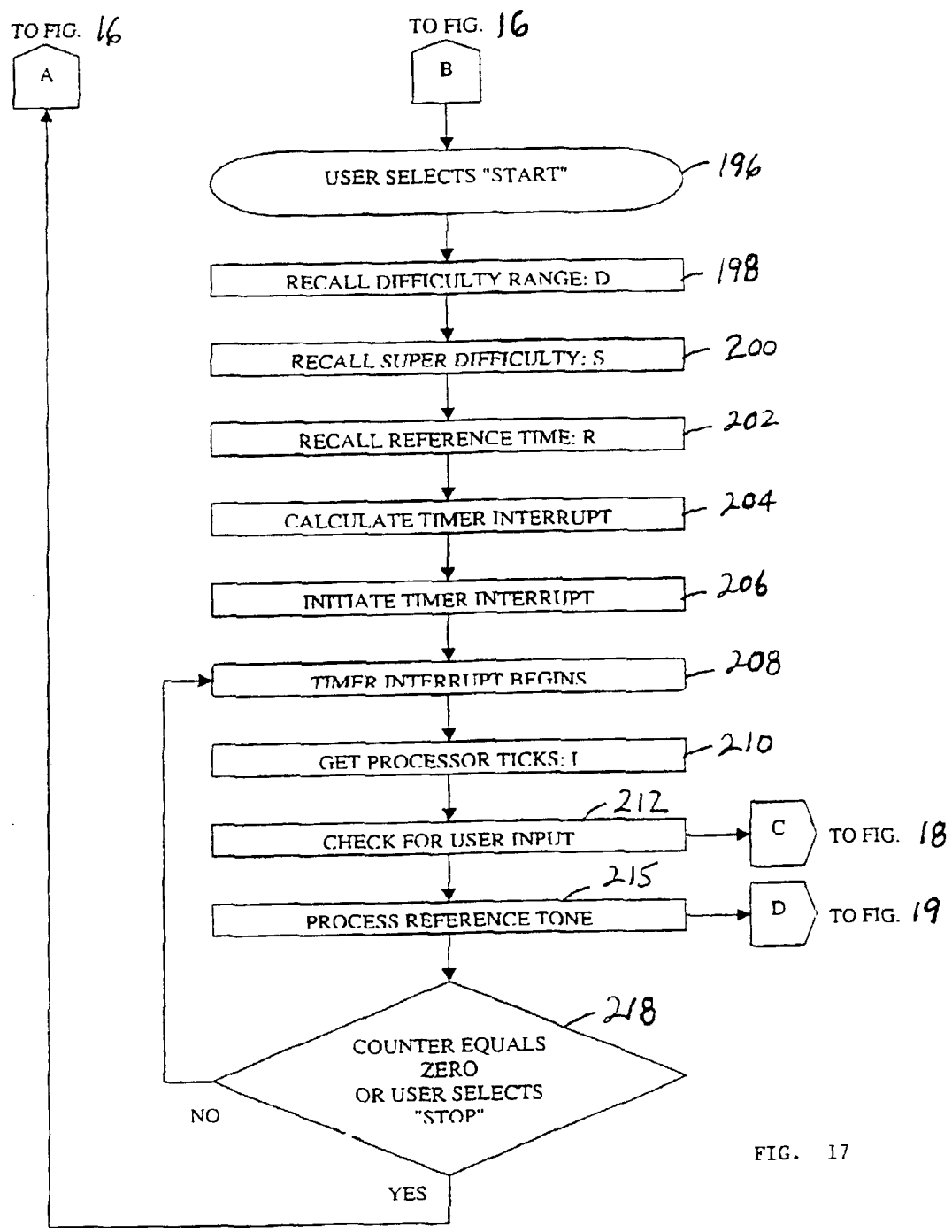
FIG. 17 is a flowchart of a timing interrupt processing function.
Figure 18:
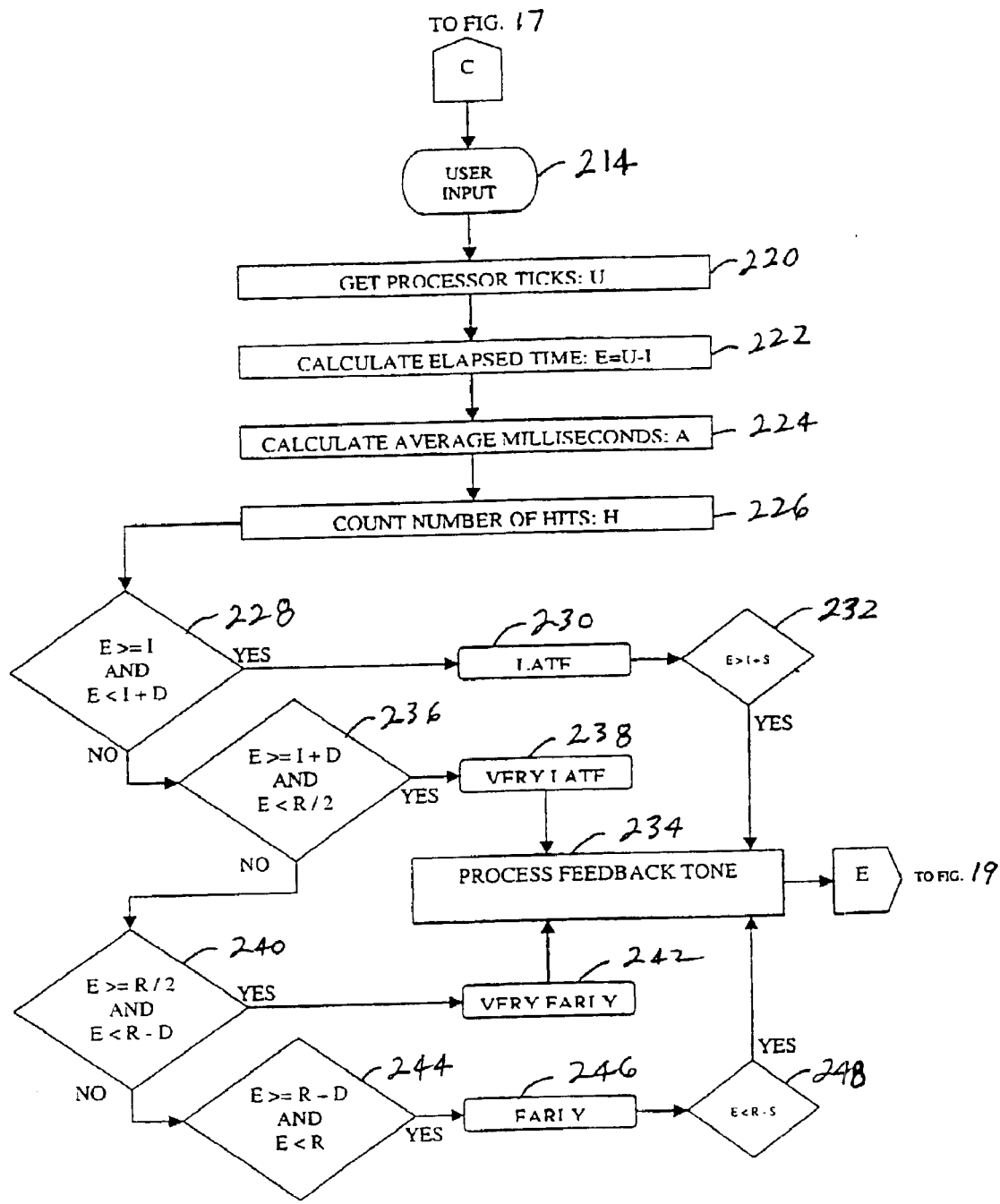
FIG. 18 is a flowchart of a temporal evaluation function.
Figure 19:
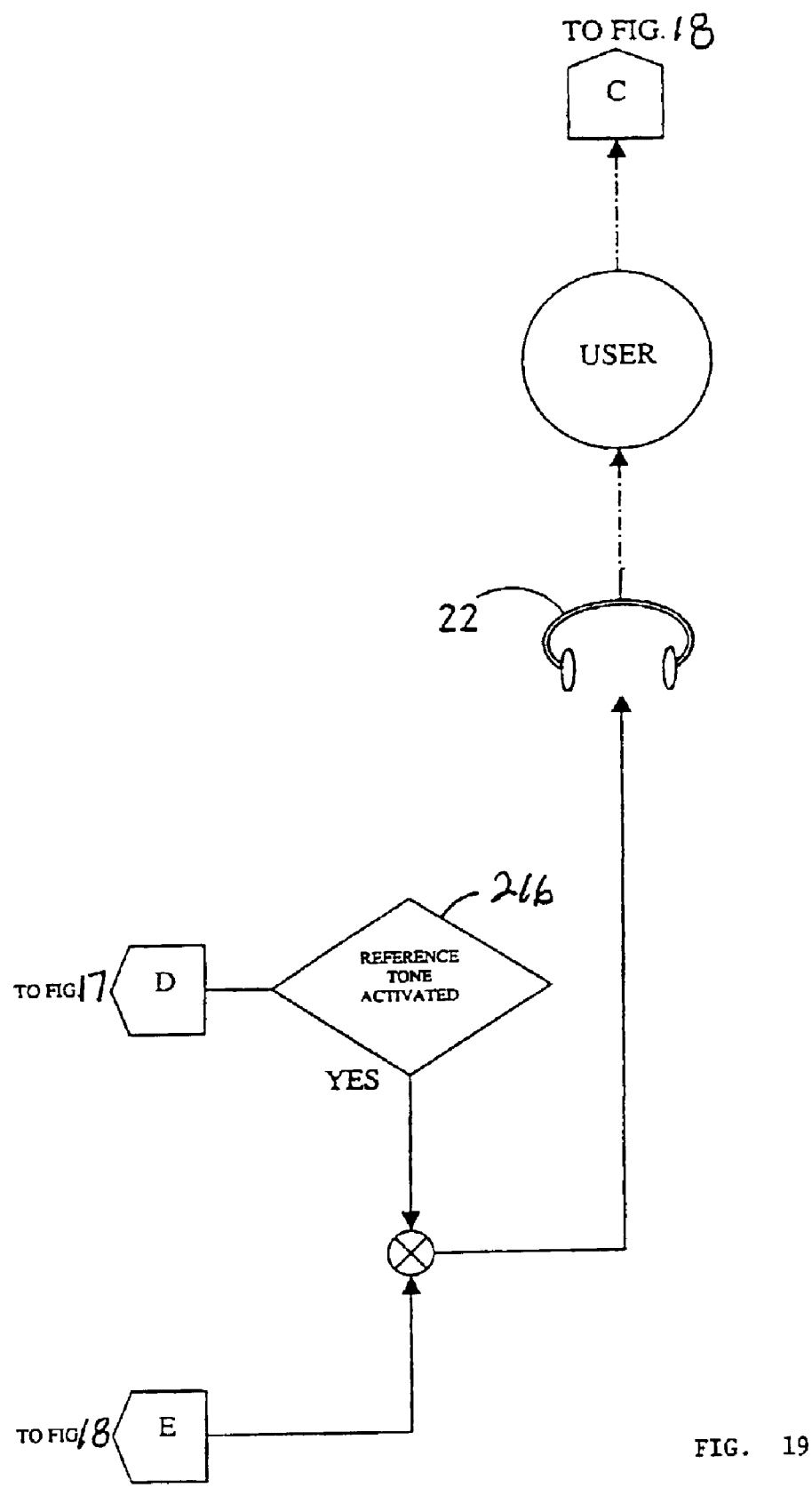
FIG. 19 is a flowchart of a user signal generation function.

Program 164 then performs a timing interrupt processing function (FIG. 17). When the user, or trainer, selects a "start" function at 196, the computer recalls parameters D, S and R from memory at 198, 200, 202 and calculates the value of I based upon the recalled parameters at 204. At 206, 208, the timer interrupt is initiated and the program begins at I (210). The program then checks for a user actuation of a trigger (18a, 18b) at 212. If a user input is received at 212, the user input is processed at 214 (FIG. 18). If a user response is not received at 212, the program determines at 215 whether it is time to generate a reference signal. If it is determined at 215 that it is time to generate a reference signal, then the program proceeds to FIG. 19 where it is determined at 216 whether the reference signal (ON/OFF) is activated. If the reference signal function is activated at 216, then a reference signal is generated, such as with headphones 22, and supplied to the user.

It is then determined at 218 whether a counter has decremented to zero or the trainer selects a "stop" function. The counter is set at the beginning of each mode and typically has a length that is a function of the mode selected. If the counter has not equaled zero, the program proceeds to 208 where another tick is processed at 210 and the program checks for user inputs (212) and processes references tones (215). When it is determined at 218 that the counter equals zero or the trainer selects the "stop" function, the program returns to the mode choosing display screen (180).

A temporal relationship evaluation function is carried out at FIG. 18. When a user input is received at 214, the program reads the value of the processor ticks (U) at 220 and calculates an elapsed time parameter (E=U−I) at 222. At 224, a parameter A is updated. A is the average response, maintained in milliseconds, of the user with respect to the reference signal. The value of A may be displayed on monitor 14 for the purpose of monitoring by the therapist and recording in a database. Although the use of an average response is illustrated, the database may store every response by the user in milliseconds early or milliseconds late. A parameter H is updated at 226. H is the number of user inputs conducted during the particular test.

It is then determined at 228 whether the value of E is greater than or equal to I and less than I+D. If so, it is determined at 230 that a late response has been received. It is then determined at 232 whether the parameter E is greater than I+S. If so, a guidance signal is generated at 234 and supplied to headphones 22 if the particular mode calls for the presentation of guidance signals to the user. Preferably, guidance signals are generated during an optional training mode 188, but not generated during short-form and long-form testing modes 184 and 186. If it is determined at 232 that the value of E is not less than I+S, a late response within the super difficulty range was received. Preferably, no guidance signal is generated for a response falling within the super difficulty range, even if the particular mode calls for the presentation of guidance signals to the user. This provides an indication to the user, who would hear only the reference signal and no guide signal, that the user has produced a response in the super difficulty range.

If the requirements of 228 are not met, it is determined at 236 whether E is greater than I+D and less than R/2. If so, the user response is determined to be very late at 238 and an appropriate guidance signal is generated at 234 if the particular mode calls for the generation of guidance signals. If the condition of 236 is not met, it is determined at 240 whether E is greater than R/2 and less than R−D. If so, it is determined that a very early response is received at 242 and an appropriate guidance tone will be generated at 234 if guidance tones are being generated. If the condition at 240 is not met, it is determined at 244 whether E is greater than R−D and less than R. If so, it is determined at 246 that an early response has been received and it is determined at 248 whether the response is prior to the super difficulty range. If so, an appropriate guidance tone is generated at 234 if guidance tones are being generated. If it is determined at 248 that E is between R−S and R, no guidance tone is generated even if guidance tones are being generated. This is an indication to the user that the user's response is within the super difficulty range.

As can be seen, learning capacity enhancement apparatus 10, 10', 10'', 40, 40', 60*a*, 60*b* and 80 provide the ability of teaching users, including young children, learning skills without involving the overt or surface behavior of the user. This is especially important in enabling a very young child who is not yet able to perform overt surface behavior tasks to obtain the benefits of the techniques described in my previous patents. It accomplishes this by appealing to the desire of the user to learn and to respond to stimuli that are exciting to the user. It also rewards the user when the user performs constructive patterns of motion. Apparatus 40, 40', 60*a*, 60*b* and 80 could be combined with other devices, such as stuffed animals, mobiles, or the like, in order to further enhance the usefulness of the apparatus. Apparatus 40, 40', 60*a*, 60*b* and 80 provide enhancement of reward to the child the longer they attend. This increases the ability of the child to recruit and maintain the multi-tasking functions of the brain. Apparatus 10, 40, 40', 60*a*, and 60*b* may also be used with the NEUROLOGICAL CONFLICT DIAGNOSTIC METHOD AND APPARATUS disclosed in commonly assigned application Ser. No. 60/219,321, filed on Aug. 13, 1999, the disclosure of which is hereby incorporated herein by reference.

Figure 10:
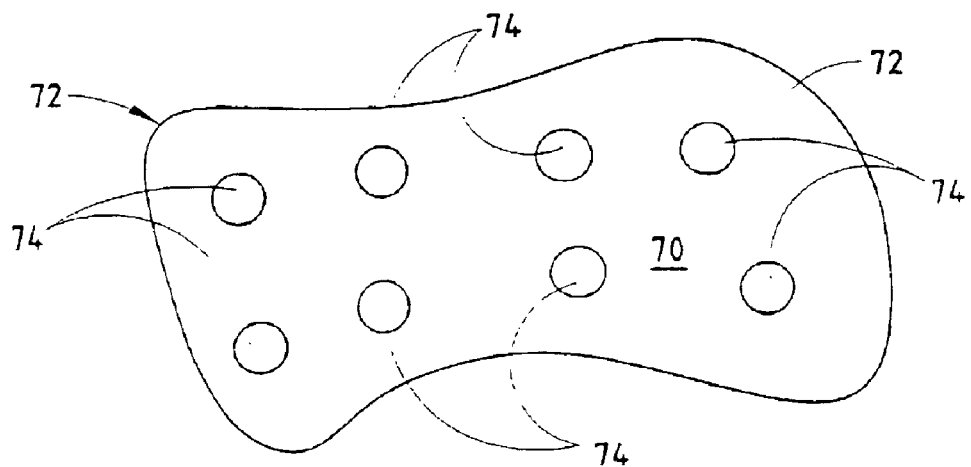
FIG. 10 is a top plan view of an alternative trigger device.

Other variations will suggest themselves to the skilled artisan. A learning capacity enhancement apparatus 70, as shown in simplified form in FIG. 10, has a trigger 72 made up of a series of sub-triggers 74. The remaining portion of the apparatus is not shown, but may be as illustrated in FIG. 1. The user may be provided with a pattern of sub-triggers 74 and instructed to operate the sub-triggers in a particular pattern that is as close as possible to a reference signal. The reference signal could be provided to the user as an aural or visual signal or could be an internal signal not supplied to the user. As the user succeeds in manipulating sub-triggers 74 according to a pattern as close as possible to the reference, a reward is provided for successful outcome in a manner that will be apparent to the skilled artisan.

In all cases of apparatus 10, 10', 10'', 40, 40', 60*a*, 60*b*, 70 and 80, the reference signal may be generated internally by the control independent of movement of the user or may be generated in response to a sequence of prior movements by the user. For example, a user may manipulate the trigger from 2 to 10, or more, times without a reference signal. The control analyzes the manipulations and creates a reference signal based upon the average occurrence interval, or tempo, of the user's previous manipulation. The control may continually adjust the reference signal as the tempo of the user's manipulation average changes. The guide sounds may be supplied to the user to improve the ability of the user to stay with the reference signal which the user is influencing with his/her manipulation of the trigger. This same principle may be used with two or more users who manipulate individual triggers as part of an interactive group using the combined average of the trigger manipulations by the group to establish the tempo of the reference signal. Alternatively, only one person in the group may be used to control the tempo of the reference signal. The reference signal may be supplied at all times to the user or may be interrupted periodically to allow the user to respond strictly to the internal timing mechanism of the user. The reference and guidance signals may be generated either aurally, visually, or a combination of both.

Changes and modifications in the specifically described embodiments can be carried out without departing from the principles of the invention which is intended to be limited only by the scope of the appended claims, as interpreted according to the principles of patent law including the doctrine of equivalents.

EXHIBIT A

AJOT Assignment #99-131

Effect of Interactive Metronome® Training on Children with ADHD

Robert J. Shaffer, Ph.D.

Adjunct Assistant Professor of Pediatrics & Human Development

College of Human Medicine

Michigan State University

Lee E. Jacokes, Ph.D.

Professor of Psychology

Aquinas College

James F. Cassily, Director (Corresponding Author)

Neural Technology Research Center

3090 Dawes SE

Grand Rapids, Mich. 49508

616-246-1301

Email—cassily@interactivemetronome.com

Stanley I. Greenspan. M.D.

Clinical Professor of Psychiatry, Behavioral Sciences, and Pediatrics,

George Washington University Medical School

Robert F. Tuchman, M.D.

Professor of Neurology

University of Miami Medical School

Miami Children's Hospital

Paul J. Stemmer, Jr., Ph.D.

Madonna University

KEYWORDS

Motor Planning and Sequencing
Technology

INTERACTIVE METRONOME EFFECT

The ability to attend, which begins early in life, is a vital part of the capacity to learn, concentrate, think, interact with others, and master basic academic skills (Greenspan & Lourie, 1981; Greenspan, 1997; Mundy & Crowson, 1997). Relative deficits in sustaining attention, inhibiting competing impulses, and engaging in joint attention can be found in attentional, learning and developmental disorders. These deficits are part of several clinical disorders, including Attention Deficit Disorder (ADD), Pervasive Developmental Disorder (Autistic Spectrum Disorders), language disorders, motor disorders, and specific learning disorders involving reading, math, and writing (Mundy, 1995; Barkley, 1997a).

Increasing evidence suggests that broad constructs such as motor planning and sequencing, rhythmicity, and timing are relevant to attentional problems. Deficits in inhibition and executive functions, which involve the regulation and sequencing of motor patterns and behavior, are postulated by Barkley (1997b) to be important in understanding attention-deficit/hyperactivity disorder (ADHD). Important relationships between attention and aspects of motor regulation, including inhibition (Schonfeld, Shaffer & Barmack, 1989), speed, rhythm, coordination, and overflow has been postulated by several investigators (Barkley, Koplowitz, Anderson & McMurray, 1997; Denckla, Rudel, Chapman & Krieger 1985; Piek, Pitcher & Hay, 1999). Gillberg (1988) has described a group of children with deficits in attention, motor control, and perception, termed DAMP syndrome, and, in a recent study Kadesjo (1998) found considerable overlap between attention deficits and motor clumsiness. In this group of children, the combination of both attentional and motor problems tends to worsen the prognosis (Hellgren, Gillberg, Gillberg & Enerskog, 1993; Hellgren, Gillberg, Bagenholm & Gillberg, 1994). Piek (1999) has recently demonstrated that the severity of inattentive symptomatology in ADHD boys is a significant predictor of motor coordination difficulties. Furthermore, recent work suggests that approximately half of all children with developmental coordination disorder (DCD) have moderate to severe symptoms of ADHD, and a diagnosis of DCD at age 7 years was associated with restricted reading comprehension at age 10 years (Kadesjo & Gillberg, 1999).

According to the Developmental, Individual-Difference, Relationship (DIR) model (Greenspan 1992; Greenspan & Wieder, 1999) which uses dynamic systems theory (Smith & Thelen, 1993; Gray, Kennedy & Zemke, 1996a, 1996b) to understand children's adaptive and maladaptive behavior, a child brings a variety of unique processing capacities, including motor planning and sequencing, into interactions with others and the physical environment in order to construct complex adaptive patterns such as attending to and carrying out multi-step actions in school and at home. Furthermore, there is considerable overlap in the neural networks involved in ADHD and the regulation of timing and the motor planning. These networks involve prefrontal and striatal regions of the brain. A recent study using Functional MRI evaluation demonstrated that children with ADHD had subnormal activation of prefrontal systems responsible for high order motor control (Rubia, et al., 1999).

The relationship between motor regulation and attentional and executive functions suggests that technologies aimed at strengthening motor planning, sequencing, timing, and rhythmicity may have a role in improving the capacity to attend and learn (Greenspan, 1992). The Interactive Metronome®, a patented PC-based interactive version of the traditional music metronome, developed in 1992 (Cassily, 1996), provides a new educational technology aimed at facilitating a number of underlying central nervous system processing capacities hypothesized to be involved in motor regulation. Non-interactive metronomes have been used as temporal teaching tools since being invented in 1696 by Étienne Loulié. The Interactive Metronome® (IM) is the first to utilize the capabilities of modern computers to add an interactive element to this traditional tool. Instead of users having to rely on their own mental estimations of their own temporal accuracy, the IM provides users with accurate (to .5 ms.) real-time guide sounds to indicate their temporal accuracy as they perform a series of prescribed movements. The tonally and spatially changing guide sounds enable users to deliberately correct their planning and sequencing and timing errors as they are occurring.

Preliminary studies have shown that the level of a person's performance on the IM that involves planning, timing, and rhythmicity of motor regulation correlates with the severity of developmental, learning, and attentional problems, improvements in academic performance, and age-expected performance chances during the school years (Kuhlman & Schweinhart, 1999). Children with a range of developmental and learning problems in special education classes who trained on the IM have demonstrated gains in motor performance in comparison to a similar group without such training who demonstrated no gains over the same period of time. (Stemmer, 1996).

A recent study has shown that IM training can improve motor control, focus, and athletic performance in golfers (Libkuman & Otani, 1999). The present study is the first controlled clinical trial of IM training on a group of children who meet the DSM-IV (APA, 1994) criteria for Attention Deficit Disorder. The purpose of this study was to determine the effects of the Interactive Metronome on selected aspects of motor and cognitive skills in a group of children diagnosed with ADHD.

THE RESEARCH DESIGN

This research used an experimental pretest, posttest measurement design. (See FIG. 1.)

FIG. 1 The Experimental Research Design
TREATMENT GROUPS

| Interactive Metronome ®<br>N = 19 | Control Group<br>N = 18 | Video Group (Video)<br>N = 19 |
| --- | --- | --- |
| Pretesting | Pretesting | Pretesting |
| IM Training Period | No Activity | Video Training Period |
| 15 One Hour Sessions | | 15 One Hour Sessions |
| over a Three Week Period | | over a Three Week Period |
| Posttesting | Posttesting | Posttesting |

SAMPLE

The subjects were drawn from the population of ADHD boys, age 6 to 12 years, within the greater metropolitan area in which the study was conducted. Seventy-five volunteers with verification of a clinical diagnosis by their pediatricians, pediatric sub-specialists, and/or psychologists/psychiatrists as meeting DSM IV criteria for Attention Deficit Hyperactivity Disorder were recruited through local school districts, physicians, psychologists, psychiatrists, and advertising in a local newspaper. Test administrators screened and pre- and posttested each child who was randomly assigned to them. All testing and treatments were given at no cost to the parents of the subjects. All test administrators were paid, qualified psychometricians or licensed occupational therapists (OTRs) certified in administering their respective tests. Test administrators were not informed about the study's purpose and were blind as to who received what treatment.

As a result of the above screening, 19 subjects were dropped from the volunteer pool, either because they did not meet the clinical or research criteria or had severe learning, cognitive deficits, neurological, anxiety or depression problems. Demographically, the 56 qualified participants in this group was 6 to 12.5 years old, 86% Caucasian, and 14% other races. Thirty-two percent had parents or guardians with incomes under $40,000, 38% from $40,000 to $69,000, and 30% with $70.000 or more incomes. Eighty percent of subjects had parents or guardians with a college education.

Both parents and children were told the purpose of the study was to "explore the use of non-pharmacological methods in the treatment and management of ADD/ADHD" and that the "treatments to be used in the study were interactive computer-based treatment programs." They were told that all participants would eventually receive all treatments. No further information about the study was provided until completion of treatment and posttesting. One subject was belligerent toward his administrator and was removed from study after the second day. After completion of the study the participants of both the Video and the Control group received the IM treatment.

INSTRUMENTATION

Four major categories of performance were targeted for assessment. The assessment instruments were selected from those most commonly used by the psychological, occupational therapy and educational communities. Only assessment instruments that have been shown to be reliable and valid were used (see reference for each instrument). Summary and subtest scores from the following instruments were used to assess these areas:

ATTENTION AND CONCENTRATION

1) Tests of Variables of Attention (TOVA), a 25-minute computer based test, is one of the most widely used objective measures of ADHD (Greenburg & Dupuy, 1993). 2) Conners' Rating Scales—Revised (CRS—R) Teacher and Parent Versions, a questionnaire completed by the parents and teachers, is one of the most widely used subjective measures of ADHD (Conners, 1990). 3) Wechsler Intelligence Test for Children—$3^{rd}$ Edition (WISC-III) is a well-known and widely accepted test of intelligence for children (Wechsler, 1992). 4) Achenbach Child Behavior Checklist, a questionnaire completed by parents, measures internalized problems and external behaviors (Achenbach, 1991).

CLINICAL FUNCTIONING

1) Conners Rating Scale. 2) Achenbach Child Behavior Checklist 3) The Sensory Profile—assesses auditory, visual, activity level, taste/smell, body/position, movement, touch, emotional/social functioning (Dunn & Westman, 1995). 4) Bruininks-Oseretsky Test for Motor Efficiency (B-O) (Selected subtests) assesses bilateral coordination, upper-limb coordination and upper-limb speed and dexterity (Bruininks, 1978).

ACADEMIC AND COGNITIVE SKILLS

1) Wide Range Achievement Test—3 (WRAT 3) (Reading and Writing) assesses reading decoding, spelling and math computation. 2) Language Processing Test (LPT) assesses basic language (Wilkinson, 1993).

Subjects were pre- and posttested at the same time of the day to control for medication schedules and circadian rhythms. On tests that offered equivalent forms, a different form was utilized for the posttesting then for the pretesting. The period between pre- and posttesting was 4 to 5 weeks.

IM TREATMENT AND VIDEO TREATMENT CONTROL GROUP ADMINISTRATORS

The IM and Video group participants were randomly assigned to paid administrators that treated participants of both groups. The administrators were college graduates, students, and/or individuals without advanced degrees, and with no previous formal therapy and teaching. Each administrator received an equal six hours of instruction on both the IM and on the video games.

Environments and treatment schedules for both the IM and Video groups were matched. Administrators followed a daily treatment regimen guide booklet for subjects in both groups that controlled the structure of the sessions, time spent in conversation and the amount of encouragement given. Subjects were asked not to share their experiences with other subjects.

TREATMENTS—INTERACTIVE METRONOME® AND VIDEO GAMES

Interactive Metronome® Apparatus

The patented IM apparatus used in the study included a Pentium computer, the IM software program, two sets of headphones, and two contact sensing triggers. One trigger, a special glove with a contact sensor attached to the palm side, sensed exactly when the triggered hand made contact with the other hand while clapping, or when one hand was tapped on the thigh. The other trigger, a flat plastic pad placed on the floor, sensed when a toe or heel was tapped upon it.

When the participant tapped a limb in time with the steady metronome reference beat sound heard in the headphones, the trigger sent a signal via a cable to the IM computer program. The IM analyzed exactly when in time the tap occurred in relation to the reference beat and instantaneously transposed the timing information into guidance sounds that the participant heard in the headphones as each tap occurred. The pitch and left to right headphone location of the guidance sounds precisely changed according to each tap's accuracy. The IM program generated planning and sequencing accuracy scores (IM scores), displayed in milliseconds on the screen, indicated to administrators how close in time the participant responses were to the reference beat as they occurred. After each exercise the participants were shown their IM scores, which appeared to motivate them to do better.

IM TRAINING

The object of the IM treatment was to help participants improve their ability to selectively attend, without interruption by internal thoughts or external distractions, for extended periods of time. Simple limb motion exercises were used as systematic outward catalysts to an underlying mental focus improvement process. Each subject underwent 15 one hour IM treatment sessions, one session per day, spread out over a 3 to 5 week period. Each session included 4 to 8 exercises that were repeated a specific number of repetitions as prescribed in a daily lesson booklet. Exercises were done at a pre-set tempo of 54 repetitions per minute and the number of repetitions per exercise increased from 200 during the first session to a maximum of 2,000 during the ninth session.

The 13 IM treatment exercises were designed to help the participants to put their efforts toward improving mental concentration, rather than developing new physical motion techniques. The exercises included: clapping both hands together, tapping one hand alone against the upper thigh, alternating toe taps on the floor trigger, alternating heel taps, tapping one toe or heel alone, alternating between tapping one hand on the thigh and the other toe on the floor trigger, and balancing on one foot while tapping the other toe.

Before beginning their first IM treatment session, IM participants were given an automated IM pretest to quantify their ability to recognize timing patterns, selectively attend to a task and make simple motion corrections. The IM pretest also indicated if they had one or more planning and sequencing deficiency patterns that needed to be addressed during their initial stage of IM treatment. IM treatment regimens were designed and accomplished in stages according to instructions in the daily training guide book.

During the first stage, the administrators helped the participants break the existing planning and sequencing deficiency patterns that were identified during their IM pretests. The six planning and sequencing deficiency patterns most frequently identified were: (1) Disassociative the responses were chaotic and random and not related to the beat whatsoever—3 subjects); (2) Contraphasic (within a few beats, the subject's responses consistently moved to in-between the beat rather than on beat—6 subjects); (3) Hyperballistic (the subjects utilized inappropriate snappy ballistic type motions—16 subjects): (4) Hyperanticipatory (the responses continually occurred way before the reference beat—18 subjects); (5) Hypoanticipatory (the responses continually occurred way after the reference beat—1); (6) Auditory Hypersensitivity (the subjects were exceptionally distracted by the computer generated guide sounds that were added to the headphone mix during the last test task, as indicated by their IM ms. scores on that task being two to three times less accurate then the previous 13 tasks done without the guide sounds—7 subjects).

The initial IM treatment sessions were devoted to helping the participants learn how to discriminate between the sounds triggered by their own actions and of the steady IM metronome beat sound. They were instructed to make smooth, controlled hand and foot motions that continually cycled through a repeating pattern without stopping at any time in between beats. Participants were repeatedly instructed to focus on the metronome beat and to try not to be interrupted by their own thoughts or things happening around them. When the participants had broken their existing planning and sequencing patterns, and were able to achieve the IM millisecond score average prescribed in the regimen booklet, they were considered to have achieved adequate control and accuracy necessary to begin a second distinct phase of the IM treatment program.

During the second IM treatment phase participants were instructed to focus their attention only on the steady reference beat and ignore their own trigger generated guide sounds, internal thoughts and the unrelated stimuli around them. The were also instructed to keep repeating their motion patterns without making any deliberate adjustments whatsoever. Doing so usually resulted in obvious improvements in the participant's IM score, and the entrainment experience of staying on-beat without trying seemed to have a positive motivating effect. From session to session, participants increased the length of time they could selectively focus on the metronome beat without interruption, and their IM program scores improved correspondingly. Most of IM participants appeared to be highly motivated to achieve the best score possible during their training regimen. According to the IM Training scores, every participant in the IM group improved their planning and sequencing and were able to stay on task, without being interrupted, for significantly longer periods by the end of their training.

PLACEBO COMPUTER GAME TRAINING ACTIVITY FOR VIDEO CONTROL GROUP

Five commonly available PC-based non-violent video games were used as a treatment placebo for the Video control croup. Each involved eye-to-hand coordination, advanced mental planning, and multiple task sequencing. In each game, the subject played against the computer programming and each new level achieved became increasingly more difficult to play.

The administrators followed the daily Video group training regimen booklet in the same manner as they did the IM regimen booklet. The prescribed in the booklet provided the subjects with the same type of supervision, attention and support as was received by the IM Group. Each subject underwent 15 one-hour Video training sessions, one session per day, spread out over a 3 to 5 week period. Each training session involved a number of video game exercises, and the length of time they spent on each video game exercise typically increased from the first session to the last session.

ANALYSIS

Sampling Design and Results

Following completion of pretesting of all 56 participants, a matched random assignment process was used to form the three treatment groups. Three factors were used in the matching process: medication dosage (milligrams per body weight), age of participant, and severity of ADHD as measured by the TOVA ADHD score. These factors were chosen to control for effects of medication, developmental age differences, and severity of ADHD. An analysis of variance of these three matching variables revealed no significant differences at the $p \leq 0.05$ level of significance among the three comparison groups. Chi-Square analysis of three demographic variables, race of subject, parental education, and parental household income, revealed no statistically significant differences at the $p \leq 0.05$ level, suggesting the three comparison groups are equal for these socioeconomic factors.

Analysis of variance of the 58 pretest factors revealed that there was only one statistically significant difference between the three comparison groups. Sakoda's (1974) table for tests of significant difference revealed the probability of this one significant difference in 58 significance tests occurring by chance to be $p > 0.50$, establishing this single occurrence to be likely a chance difference. The other 57 factors produced p values in excess of $p > 0.05$, establishing the comparison groups' statistical equality.

PATTERN ANALYSIS

Pattern analysis of the 58 test scores examined the overall direction of mean differences between pre- and post-test phases for each group. In performing the analysis, the means (Pretest=P1 and the Posttest=P2) for each test were computed and the mean differences between P1 and P2 were determined. Each mean difference was dichotomized by whether the change represented an improvement or a decline in the desired direction for that test. For example, the P2–P1 mean differences for the Wechsler Digit Span sub-test for each of the three groups were IM=+0.473, Control=−0.278 and Video=−0.054. The mean differences revealed improved performance in the IM group while the Control and Video groups showed decreased performance. Similar analyses were completed for all 58 test scores.

To statistically test the pattern, a binomial test was used to determine whether the proportion of dichotomous pairs (improvement vs. decline) was likely a chance occurrence (where the probability of either an improvement or decline is equal to 0.50) or whether the directional proportion was so unusual as to reflect a non-chance event. The rationale for using a binomial test rests on the assumption that if a large number of variables collectively showed an unusual directional propensity, for example, improved performance, this represented an overall pattern of change worthy of notice. The binomial test allows detection of a combined directional pattern which individual variables, taken one at a time, does not detect.

The pattern analysis revealed the following. The Control group had 28 scores improve and 30 decline. Such a result has a high probable chance occurrence of $p = 0.8955$ and suggests that no statistically significant combined directional pattern is present (Norusis, 1993). Analysis of the IM and Video groups produced statistically significant improvement/decline patterns. For the IM group, 53 of the 58 variables showed improvement ($p \leq 0.0001$). For the video group, 40 of 58 variables showed improvement ($p \leq 0.0058$). Both groups showed statistically significant pattern increases in performance over the Control group. The IM group experienced significantly better improvement than the Video group, suggesting the IM treatment produced statistically significant additional benefits above and beyond the experience of the Video control group participants.

SIGNIFICANT DIFFERENCE ANALYSIS

The pattern analysis identified the overall improvement/decline characteristics of the test mean differences but did not address the magnitude of these differences. Since a pretest/posttest repeated measurements design was utilized, an analysis of variance for repeated measures (SPSS, 1988) was performed separately on each of the 58 variables. This approach was chosen in order to view the effects of the three treatment groups on each test score individually. However, one possible disadvantage of the approach is its potential of increasing Type 1 error.

Of the 58 test score analyzed, twelve either had statistically significant interaction effects (p vales ranging from 0.047 to 0.0001), suggesting some combination of treatments and sub-group means were different and/or there were statistically significant pre- posttest differences. Twelve significant differences out of 58 significance tests had a $p \leq 0.001$ (at the 0.05 level of confidence. Sakoda. 1974), suggesting these differences are not chance differences. Additionally, Keppel's (1973) calculation for the potential number of Type 1 errors over 58 separate experiments is 2.9. Thus, these twelve statistically significant differences far exceed the calculated potential of 2.9 Type 1 errors suggesting these differences are real statistically significant differences.

Among the above statistically significant effects, seven statistically significant differences between-phases effects were found (p values ranging from 0.023 to 0.0001). This analysis finds the IM treatment group statistically significantly improving their performance in identifying similarities and differences between concepts and experiencing declines in aggressive behavior as reported by their parents. Both the IM and Video treatments produced statistically significant improvements on three Sensory Profile sub-tests, suggesting both groups benefited from the attention and activities provided in these treatments. Parental reports on the Child Behavior Checklist also revealed statistically significant declines in aggressive behavior for the IM group, a non-statistically significant improvement for the Video group, and no improvement for the control group.

The remaining five tests had significantly different interaction effects (p values between $p = 0.0001$ to 0.047). These five tests included the WRAT-3 Reading subtest and four tests of The Variables of Attention (TOVA) including Omissions, RT Variability, RT Variability Total-STD Deviation, and the ADHD Total Score. The significant interaction effects suggest the posttest IM performances, though not significantly improved over the pretest performances, non-the-less showed statistically significant higher performances compared to the posttest performances of the Control and Video treatments. For all five tests, the patterns of differences were identical: IM performances improved while both Control and Video performances declined.

In summary, the pattern analysis revealed that both IM and Video groups experienced statistically significant improvement patterns across the 58 test scores. Additionally, the IM Group had a statistically significantly stronger improvement pattern than the Video group showing improvements over 53 test score compared to 40 for the Video group. This supports the hypothesis that IM training produced a stronger improvement pattern than was true for the Video group for male children with ADHD difficulties.

Analysis of test means found 12 factors with statistically significant quantitative changes among the various group and treatment combinations. The IM group showed statistically significant pre- post test improvement in identifying similarities and differences and reduction of aggression problems compared to the other two treatment groups. Both the IM and Video groups showed statistically significant improvements in three sensory processing tasks and in parental reports of impulsive/hyperactivity. Only parents of the IM subjects, however, rated their children as statistically significantly less aggressive ($p \leq 0.001$) after the treatment period than parents in the other two groups. Additionally, five tests measuring reading and four characteristics of attention revealed the IM group with statistically significantly higher posttest performances compared to the performances for the other two treatment groups.

DISCUSSION

The results indicated that boys with ADHD who received the IM intervention improved significantly more in areas of attention, motor control, language processing, and reading, and in their ability to regulate aggression than boys receiving either the Video treatment or no-intervention Control group. Those who received Video game coaching improved more than the control group on a number of measures as well, demonstrating that focused perceptual activities and support alone may be helpful for selected areas of functioning. The Video group, however, also evidenced decreased performance in selected areas, involving modulation and control, such as consistency of concentration, reaction time, and overall attention.

IM training, on the other hand, only evidenced improved performance including statistically significant positive gains over the Video treatment group on a series of TOVA attentional tasks measuring lack of errors and distractibility, consistency of reaction time, and overall attention; selected language (i.e., similarities and differences), academic tasks (reading); and control of aggression. In addition, pattern analysis was used to control for the effect of using a large number of assessments and demonstrated that the differences between the patterns in the groups were statistically significant. The NIH Consensus Statement (1997) asserts that studies on ADHD interventions must properly control for the positive overall effect of attentive adult interaction, alone. Consistent with NIH guidelines, two of the three groups in this study received adult attention during the treatment period.

Methodological considerations and limitations of this study include the following. Only males in a defined age-range were included to minimize age and gender variation, limiting generalizing the results to females, as well as other ADHD male age groups. The variables measured by the assessments are limited to selected aspects of attention, motor control, language, cognition, and learning.

In this study, IM training influenced a number of performance capacities. A possible explanation for the positive changes is the central role of motor planning and sequencing in each of these performance areas. In a dynamic systems model (Smith & Thelon, 1993), critical variables, such as the ability to plan and sequence actions may influence a broad array of adaptive functions including attention. (Greenspan. 1992).

The results of the current study suggest directions for further research, including replications of the current study on larger populations (which might permit the identification of characteristics associated with different patterns of response to metronome training), on females, and on more socioeconomically diverse populations to observe potential components of different environmental contexts. Further research could also investigate subgroups based on both metronome performance and the child's processing profile.

Specific variations of the IM training process also need exploring, including increasing the number of sessions, overall repetitions, timing accuracy goals, and length of follow up time (to observe stability of IM effect). In addition, further research is needed to more fully understand both the dynamic systems and the underlying central nervous system mechanisms involved in motor regulation and the way in which IM training influences these processes. The IM may be the first technology that can allow the creation of a database and classification of "timing" that will help compare the effects of interventions that influence timing in a variety of perceptual motor processes.

In conclusion, from a dynamic systems perspective (Smith & Thelen, 1993; Gray, et al., 1996a, 1996b), many processes, including the timing and rhythmicity of motor behavior, influence motor planning. In turn, motor planning interacts with other factors, including learning opportunities and environmental demands, to influence patterns of self-regulation and functioning in home, school, and with peers. Until recently, interventions to strengthen these capacities have been limited to working with overt or surface behavior in educational or therapeutic settings. The present study suggests that IM training can improve aspects of attention, motor, and perceptual motor functioning, cognitive and academic performance, and the control of aggression in children with significant attentional problems, and, therefore, IM training may be able to complement existing interventions for these children.

REFERENCES

Achenbach, T. M., & Edelbrock, C. E. (1991). *Child Behavior Checklist*. Department of Psychiatry, University of Vermont, Burlington, Vt.

APA DSM-IV Task Force (1994). *DSM-IV Diagnostic and Statistical Manual*. Washington, D.C.: American Psychiatric Press.

Barkley, R. (1997a). Attention-deficit/hyperactivity disorder, self-regulation, and time: Toward a more comprehensive theory. *Journal of Developmental and Behavioral Pediatrics,* 18: 271–9.

Barkley, R. A. (1997b). Behavioral inhibition, sustained attention, and executive functions: constructing a unifying theory of ADHD. *Psychological Bulletin,* 121: 65–94.

Barkley, R. A.. Koplowitz, S., Anderson. T., & McMurray, M. B. (1997). Sense of time in children with ADHD: Effects of duration, distraction, and stimulant medication. *Journal of the International Neuropsychological Society.* 3: 359–69

Bruininks R. H. (1978) *Bruininks-Oseretsky test of motor proficiency: examiners manual.* Circle Pines, Minn.: American Guidance Service.

Cassily, J. F. (1996). Methods and Apparatus for Measuring and Enhancing Neural Motor Coordination. U.S. Pat. No. 5,529,498: Jun. 25, 1996.

Conners, C. K. Ph.D. (1990). *Conners' Rating Scales—Revised* (CRS—R). PAR, Psychological Assessment Resources, Inc., 22: 5f Denckla, M. B., Rudel, R. G., Chapman, C., & Krieger, J. (1985). Motor proficiency in dyslexic children with and without attentional disorders. *Archives of Neurology,* 42: 228–31.

Dunn, W., Westman, K. (1995) *Sensory profile study, occupational therapy education,* Kansas City, Kans.: University of Kansas.

DuPaul, G. J., Barkley, R. A., & McMurray, M. B. (1994). Response of children with ADHD to methylphenidate: interaction with internalizing symptoms. *Journal of the American Academy of Child and Adolescent Psychiatry,* 33: 894–903.

Gillberg, I. C. & Gillberg, C. (1988). Children with deficits in attention, motor control and perception (DAMP): need for specialist treatment. *Acta Paediatr Scand* 77: 450–451.

Gray, I. M., Kennedy, B., & Zemke. R. (1996a). Application of dynamic systems theory to occupation. In R. Zemke & F. Clark (eds.), *Occupational science: The evolving discipline* (pp. 300–324), Philadelphia: F. A. Davis.

Gray, J. M., Kennedy, B., & Zemke, R. (1996b). Dynamic systems theory: An overview. In R. Zernke & F. Clark (Eds.), *Occupational science: The evolving discipline* (pp. 297–308). Philadelphia: F. A. Davis.

Greenberg, L. M. & Dupuy, T R. (1993). *Interpretation manual for the Test of Variables of Attention computer program.* (Available from Universal Attention Disorders, 4281 Katella Avenue, #215, Los Alamitos, Calif. 90720)

Greenspan, S. I. (1992). *Infancy and Early Childhood: The Practice of Clinical Assessment and Intervention with Emotional and Developmental Challenges.* Madison, Conn.: Internat. Univ. Press.

Greenspan, S. I. (1997). *The Growth of the Mind and the Endangered Origins of Intelligence.* Reading, Mass.: Addison Wesley Longman.

Greenspan, S. I. and Lourie, R. S. (1981). Developmental structuralist approach to the classification of adaptive and pathologic personality organizations: Application to infancy and early childhood. *American Journal of Psychiatry,* 138:6.

Greenspan. S. I & Wieder, S. (1999). A functional developmental approach to autism spectrum disorders. *Journal of the Associaiion for Persons with Severe Handicaps* (JASH), 24: 147–161.

Hellgren, L., Gillberg, C., Gillberg, I. C., & Enerskog, I. (1993). Children with deficits in attention, motor control and perception (DAMP) almost grown up: general health at 16 years. *Developmental Medicine and Child Neurology,* 35: 881–92.

Hellgren, L., Gillberg, I. C., Bagenholm. A., & Gillberg, C. (1994). Children with deficits in attention, motor control and perception (DAMP) almost grown up: psychiatric and personality disorders at age 16 years. *Journal of Child Psychology and Psychiatry and Allied Disciplines.* 35: 1255–71.

Kadesjo, B. & Gillberg, I. C. (1998). Attention deficits and clumsiness in Swedish 7-year-old children. *Developmental Medicine and Child Neurology,* 40: 796–804.

Kadesjo, B. & Gillberg, I. C. (1999) Developmental coordination disorder in Swedish 7-year-old children. *Journal of the American Academy of Child and Adolescent Psychiatry,* 38: 820–8

Keppel, G. (1773). *Design & Analysis: A Researcher's Handbook.* Englewood Cliffs, N.J.: Prentice-Hall, Inc., p 87.

Kuhlman, K. & Schweinhart, L. J. (1999). Timing in child development. Ypsilanti, M I: High/Scope Educational Research Foundation. In press.

Libkuman, T. & Otani, H., (1999) *Training in Timing Improves Accuracy in Golf.* Unpublished manuscript. Mt. Pleasant, Mich.: Central Michigan University.

Mundy, P. (1995). Joint attention and social-emotional approach behavior in children with autism. *Developmental Psychopathology,* 7: 63–82

Mundy, P., & Crowson, M. (1997). Joint attention and early social communication: Implications for research on intervention with autism. *Journal of Autism and Developmental Disorders.* 27: 653–76

NIH Consensus Statement (1997) *Archives of General Psychiatry,* 54: 865–70.

Norusis, M. (1993). *SPSS for windows, base system, user manual, release* 6.0. pp. 392–393. Chicago: SPSS, Inc.

Piek, J. P., Pitcher, T. & Hay, D. A. (1999). Motor coordination and kinaesthesis in boys with attention deficit-hyperactivity disorder. *Developmental Medicine and Child Neurology,* 41: 159–65.

Rubia, K., Overmeyer, S., Taylor, E., Brammer, M., Williams, S., Simmons, A. & Bullmore, E., (1999). Hypofrontality in Attention Deficit Hyperactivity Disorder During Higher-Order Motor Control: A Study With Functional MRI. *American Journal of Psychiatry,* 156: 891–896.

Sakoda, J. M., Cohen, B. H., & Beall, G., (1974). Test of significance for a series of statistical tests. *Psychological Bulletin.* 51: 172–175.

Schonfeld, I., Shaffer. D., & Barmack, J. (1989). Neurological soft signs and school achievement: the mediating effects of sustained attention. *Journal of Abnormal Child Psychology,* 17: 575–96.

Smith, L. B., & Thelen, E. (Eds.) (1993). *A dynamic systems approach to development: Applications.* Cambridge. Mass.: MIT Press.

Stemmer, P.M. (1996). *Improving Student Motor Integration by Use of an Interactive Metronome.* Study paper presented at the 1996 Annual Meeting of the American Educational Association, Chicago, Ill.

SPSS. (1988), *SPSS-X-Users Guide,* $3^{rd}$ Ed. P. 576. Chicago. Ill.: SPSS, Inc.

Wechsler, D. (1992) *WISC-III, Wechsler Intelligence Scale for Children-Third Edition Manual.* San Antonio, Tex.: The Psychological Corporation, Harcourt Brace Jovanovich, Inc. Wilkinson, G. S. (1993) *WRAT 3 Wide Range Achievement Test Administration Manual.* Wilmington. Del.: Wide Range, Inc.

The embodiments of the invention in which an exclusive property or privilege is claimed are defined as follows:

1. A method of enhancing a user's learning capacity, comprising:

generating a reference signal having occurrences separated by time intervals;

providing a trigger and receiving from a user a manipulation of said trigger;

determining a temporal relationship between user manipulation of said trigger and an occurrence of said reference signal;

generating a guidance signal that is a function of said temporal relationship and at least occasionally presenting said guidance signal to the user; and providing a visual display and displaying a visual image with said visual display, said visual image adaptively varying in appearance as a function of user manipulation of said trigger thereby improving timing accuracy of the user beyond that achieved by user manipulation of said trigger in response to said reference signal alone.

2. The method of claim 1 wherein said generating a guidance signal includes withholding the guidance signal from the user for user manipulation of said trigger that are within a particular range, said particular range encompassing an occurrence of said reference signal.

3. The method of claim 2 wherein said guidance signal has a first characteristic for user manipulation of said trigger prior to said particular range and a second characteristic for user manipulation of said trigger after said particular range.

4. The method of claim 2 wherein said particular range extends from 15 milliseconds before to 15 milliseconds after an occurrence of the reference signal.

5. The method of claim 1 including providing stereophonic speakers and generating stereophonic aural signals with said speakers.

6. The method of claim 5 wherein said speakers comprise headphones.

7. The method of claim 3 wherein said first characteristic comprises aural signals having a directional source toward one side of the user and said second characteristic comprises aural signals having a directional source toward the other side of the user.

8. The method of claim 7 including changing the direction of the directional source with the amount of time that a user response is before or after the reference.

9. The method of claim 3 wherein said first characteristic comprises aural signals occurring in a first range of pitches and said second characteristic comprises aural signals occurring in a second range of pitches.

10. The method of claim 9 wherein the pitches of said first and second ranges are substantially collinear and separated at said particular range.

11. The method of claim 9 including generating different sounds for user manipulation of said trigger that is either much before said reference signal or much after said reference signal.

12. The method of claim 9 wherein said aural signals occurring in said first range of pitches have a directional source on one side of the user and said aural signals occurring in said second range of pitches have a directional source on the other side of the user.

13. The method of claim 1 including at least occasionally presenting said reference signal to the user.

14. The method of claim 13 wherein said reference signal is an aural signal or a visual signal.

15. The method of claim 13 including generating a reference signal having a substantially constant tempo.

16. The method of claim 13 including deriving said reference signal from prior manipulations by the user of said trigger.

17. The method of claim 1 including deriving said reference signal from prior manipulations by the user of said trigger.

18. The method of claim 1 used to enhance at least one of user attention, language processing, reading skill, and regulation of aggressive behavior.

19. An apparatus comprising:

a user operable trigger that receives user manipulation of said trigger;

a control generating a reference signal having occurrences separated by time intervals, said control determining a temporal relationship between user manipulation of said trigger and occurrences of said reference signal, said control further at least occasionally providing a guidance signal to the user that is a function of said temporal relationship;

wherein said guidance signal is withheld from the user for user manipulations of said trigger that are within a particular range, said particular range encompassing an occurrence of said reference signal.

20. The apparatus in claim 19 wherein said guidance signal has a first characteristic for user manipulation of said trigger prior to said particular range and a second characteristic for user manipulation of said trigger after said particular range.

21. The apparatus in claim 19 wherein said particular range extends from 15 milliseconds before an occurrence of said reference signal to 15 milliseconds after an occurrence of said reference signal.

22. The apparatus in claim 19 further including stereophonic speakers generating stereophonic aural signals.

23. The apparatus in claim 22 wherein said speakers comprise headphones.

24. The apparatus in claim 20 wherein said first characteristic comprises aural signals having a directional source toward one side of the user and said second characteristic comprises aural signals having a directional source toward the other side of the user.

25. The apparatus in claim 24 wherein the direction of the directional source changes with the amount of time that a user response is before or after the reference.

26. The apparatus in claim 20 wherein said first characteristic comprises aural signals occurring in a first range of pitches and said second characteristic comprise aural signals occurring in a second range of pitches.

27. The apparatus in claim 26 wherein the pitches of said first and second ranges are substantially collinear and separated at said particular range.

28. The apparatus in claim 26 wherein said aural signals include different sounds for user manipulation of said trigger that is either much before said reference signal or much after said reference signal.

29. The apparatus in claim 26 wherein said aural signals occurring in a first range of pitches have a directional source on one side of the user and said aural signals occurring in a second range of pitches have a directional source on the other side of the user.

30. The apparatus in claim 19 wherein said reference signal is at least occasionally presented to the user.

31. The apparatus in claim 30 wherein said reference signal is an aural signal or a visual signal.

32. The apparatus in claim 30 wherein said reference signal has a substantially constant tempo.

33. The apparatus in claim 30 wherein said reference signal is derived from prior manipulations by the user of said trigger.

34. The apparatus in claim 19 wherein said reference signal is derived from prior manipulations by the user of said trigger.

35. An apparatus, comprising:
- a user operable trigger which receives a user manipulation of said trigger; and
- a control generating a reference signal having occurrences separated by time intervals, said control determining a temporal relationship between user manipulation of said trigger and occurrences of said reference signal;
- wherein said control at least occasionally provides to the user a guidance signal that is a function of said temporal relationship; and
- wherein said control generates a direction signal, said direction signal indicating a desired user manipulation of said trigger relative to said reference signal.

36. The apparatus in claim 35 including an aural output providing an aural signal to the user, wherein said control supplies said reference signal at least occasionally at said aural output.

37. The apparatus in claim 35 including a visual output providing a visual signal to the user, wherein said control supplies said reference signal at least occasionally at said visual output.

38. The apparatus in claim 35 including a visual output providing a visual signal to the user, wherein said control supplies said direction signal with said visual output.

39. The apparatus in claim 35 wherein said control causes said direction signal to selectively direct a user manipulation of said trigger either before occurrences of said reference signal or after occurrences of said reference signal.

40. The apparatus in claim 35 wherein said control causes said direction signal to selectively direct a user manipulation of said trigger occasionally before said reference signal and occasionally after said reference signal.

41. The apparatus in claim 38 wherein said direction signal depicts motion in a particular direction.

42. The apparatus in claim 41 wherein said direction signal selectively directs a user to manipulate said trigger either before or after said reference signal by alternate lateral movement with respect to said depiction of motion in a particular direction.

43. The apparatus in claim 42 wherein said direction signal indicates a user's response to said direction signal.

44. The apparatus in claim 43 wherein said direction signal indicates a user's response to said direction signal as a variation of said motion in said particular direction.

45. The apparatus in claim 35 including a computer monitor, wherein said direction signal is displayed with said computer monitor.

46. The apparatus in claim 35 including a virtual reality display, wherein said direction signal is displayed with said virtual reality display.

47. The apparatus in claim 35 wherein said direction signal indicates a user's response to said direction signal.

48. The apparatus in claim 38 wherein said direction signal indicates a user's response to said direction signal.

49. The apparatus in claim 38 wherein said visual output comprises a computer monitor.

50. The apparatus in claim 38 wherein said visual output comprises a virtual reality display.

51. The apparatus in claim 35 wherein said control at least occasionally provides to the user a guidance signal that is a function of said temporal relationship and wherein said guidance signal is substantially withheld from the user for user manipulations of said trigger that are within a particular range, said particular range encompassing an occurrence of said reference signal.

52. The apparatus in claim 51 wherein said guidance signal has a first characteristic for user manipulation of said trigger prior to said particular range and a second characteristic for user manipulation of said trigger after said particular range.

53. The apparatus in claim 51 wherein said direction signal prompts the user to manipulate said trigger either prior to or after said particular range.

54. A method of enhancing a user's learning capacity, comprising:
- generating a reference signal, comprising occurrences separated by time intervals;
- providing a trigger and receiving from the user a manipulation of said trigger;
- determining a temporal relationship between manipulation of the trigger by the user and occurrence of the reference signal;
- generating a guidance signal that is a function of said temporal relationship and at least occasionally presenting said guidance signal to the user concurrently with the user's response; and
- generating a direction signal, said direction signal indicating a desired user manipulation of the trigger relative to said reference signal.

55. The method of claim 54 including substantially withholding the guidance signal from the user for user manipulations of said trigger that are within a particular range, said particular range encompassing an occurrence of said reference signal.

56. The method of claim 54 wherein said generating a direction signal includes selectively directing a user manipulation of said trigger either before the reference signal or after the reference signal.

57. The method of claim 54 wherein said generating a direction signal includes selectively directing a user manipulation of said trigger occasionally before the reference signal and occasionally after the reference signal.

58. The method of claim 54 including providing a visual display and generating said direction signal with said visual display.

59. The method of claim 58 wherein said generating a direction signal includes displaying with said visual display a depiction of motion in a particular direction.

60. The method of claim 59 wherein said generating a direction signal includes selectively directing a user's manipulation of said trigger either before an occurrence of the reference signal or after an occurrence of the reference signal as alternating lateral movement with respect to said depiction of motion in a particular direction.

61. The method of claim 60 wherein said generating a direction signal includes indicating a user's response to said direction signal.

62. The method of claim 60 wherein said indicating a user's response to said direction signal includes varying said motion in said particular direction.

63. The method of claim 54 wherein said generating a direction signal includes indicating a user's response to said direction signal.

64. The method of claim 54 including providing a visual display and generating said guidance signal with said visual display.

65. The method of claim 54 including providing an aural output and generating said guidance signal with said aural display.

66. The method of claim 54 including providing both a visual display and an aural output and including at least occasionally supplying said guidance signal at said visual display and occasionally supplying said guidance signal at said aural output.

67. The method of claim 54 including generating said direction signal with one of a computer monitor and a virtual reality display.

68. An apparatus comprising:

a trigger;

an output which provides a signal to the user; and a control for generating a reference signal having occurrences separated by time intervals and for determining a temporal relationship between user manipulation of said trigger and occurrences of said reference signal, said control causing said output to at least occasionally provide a guidance signal to the user that is a function of said temporal relationship;

wherein said trigger is at least one chosen from a body having a handle that is shaped to fit a child's hand and a member adapted to be suspended above a child's play area or sleep area.

69. The apparatus in claim 68 wherein said trigger comprises a motion sensor which responds to movement of said body.

70. The apparatus in claim 68 wherein said trigger includes a sensor which responds to movement of said member.

71. The apparatus in claim 68 wherein said output comprises at least one of an aural output and a visual output.

72. The apparatus in claim 69 wherein said control generates said reference signal from prior sequential movements of said body.

73. The apparatus in claim 72 wherein said motion sensor comprises an accelerometer or a motion-sensing circuit.

74. The apparatus in claim 69 wherein said control includes a microcomputer housed with said body.

75. The apparatus in claim 69 wherein said control is located remote from said trigger and interconnected therewith by a communication link.

76. The apparatus in claim 69 wherein said control generates said reference signal as a periodic signal irrespective of external input.

77. The apparatus in claim 69 including an orientation member responsive to said control, said orientation member orienting said body in a particular orientation as a function of said temporal relationship.

78. The apparatus in claim 77 wherein said orientation member comprises a spinning mass.

79. The apparatus in claim 78 wherein said orientation member comprises a gyroscope or a motor.

80. The apparatus in claim 68 wherein said control causes said output to produce a reward signal in response to at least one of rhythmic movement and rotational movement of said body.

81. A computer-readable medium containing program code embodying an application for a processor system having a user operable trigger and a visual display, the application performing a method of enhancing a user's learning capacity, said method comprising:

generating a reference signal having occurrences separated by time intervals;

receiving from a user a manipulation of a trigger;

determining a temporal relationship between user manipulation of said trigger and occurrence of said reference signal;

generating a guidance signal that is a function of said temporal relationship, at least occasionally presenting said guidance signal to the user; and generating a visual image with the visual display, said visual image adaptively varying in appearance as a function of user manipulation of the trigger thereby improving timing accuracy of the user beyond that achieved by user manipulation of said trigger in response to said reference signal alone.

82. A computer-readable medium containing program code embodying an application for a processor system having a user operable trigger, the application performing a method comprising:

generating a reference signal comprising occurrences separated by time intervals;

receiving from the user a manipulation of a trigger;

determining a temporal relationship between manipulation of the trigger by the user and occurrence of the reference signal;

generating a guidance signal that is a function of said temporal relationship and at least occasionally presenting said guidance signal to the user concurrently with the user's response; and generating a direction signal, said direction signal indicating a desired user manipulation of the trigger relative to said reference signal.

* * * * *

UNITED STATES PATENT AND TRADEMARK OFFICE
CERTIFICATE OF CORRECTION

PATENT NO.       : 7,122,004 B1
APPLICATION NO.  : 10/048510
DATED            : October 17, 2006
INVENTOR(S)      : James F. Cassily It is certified that error appears in the above-identified patent and that said Letters Patent is hereby corrected as shown below:

Column 1:
Line 11, "Aug.13" should be --Aug. 13--.
Lines 12-13, Delete "and provisional Application 60/489,091 filed Mar. 14, 2000" after "1999".

Column 13:
Line 34, "." after "Greenspan" should be --,--.
Line 52, Insert --:-- after "KEYWORDS".

Column 15:
Line 10, "chances" should be --changes--.

Column 16:
Line 4, "$70.000" should be --$70,000--.

Column 18:
Line 14, Insert --(-- before "the".
Line 20, ":" should be --;-- after "subjects)".

Column 19:
Line 1, "croup" should be --group--.
Line 29, "$p \leq 0.05$" should be --p0.05--.
Line 33, "$p \leq 0.05$" should be --p0.05--.

Column 20:
Line 42, "$p \leq 0.05$" should be --p0.05--.
Line 42, "." should be --,-- after "confidence"
Line 42, "." should be --,-- after "Sakoda".

Column 21:
Line 31, "$p \leq 0.05$" should be --p0.05--.

Column 22:
Line 14, "." after "Greenspan" should be --,--.

UNITED STATES PATENT AND TRADEMARK OFFICE
CERTIFICATE OF CORRECTION

PATENT NO. : 7,122,004 B1
APPLICATION NO. : 10/048510
DATED : October 17, 2006
INVENTOR(S) : James F. Cassily It is certified that error appears in the above-identified patent and that said Letters Patent is hereby corrected as shown below:

Column 23:
Line 1, "Barkley, R.A.. Koplowitz, S., Anderson." should be --Barkley, R.A., Koplowitz, S., Anderson,--.
Line 4, "." should be --,-- after "Society".
Line 10, "5.529,498" should be --5,529,498--.
Line 30, "Gray, I. M., Kennedy, B., & Zemke." should be --Gray, J. M., Kennedy, B., & Zemke,--.
Line 35, "Zernke" should be --Zemke--.
Line 53, "." after "Greenspan" should be --,--.
Line 55, "Associaiion" should be --Association--.
Line 62, "." should be --,-- after "Bagenholm".

Column 24:
Line 2, "." should be --,-- after "Disciplines".
Line 13, "M I" should be --MI--.
Line 25, "." should be --,-- after "Disorders".
Line 41, "." should be --,-- after "Bulletin".
Line 42, Delete "." after "Shaffer".
Line 44, "Abnornal" should be --Abnormal--.
Line 55, "," should be --.-- after "WISC-III".

Column 25:
Line 10, Claim 1, "guidanoe" should be --guidance--.
Line 20, Claim 2, "manipulation" should be --manipulations--.

Column 26:
Line 44, Claim 26, "comprise" should be --comprises--.

Column 29:
Line 4, Claim 68, Insert --,-- after "apparatus".

UNITED STATES PATENT AND TRADEMARK OFFICE
CERTIFICATE OF CORRECTION

PATENT NO. : 7,122,004 B1
APPLICATION NO. : 10/048510
DATED : October 17, 2006
INVENTOR(S) : James F. Cassily Page 3 of 3

It is certified that error appears in the above-identified patent and that said Letters Patent is hereby corrected as shown below:

<u>Column 30:</u>
Line 12, Claim 81, "," should be --;-- after "trigger".

Signed and Sealed this

Twenty-ninth Day of July, 2008

JON W. DUDAS
*Director of the United States Patent and Trademark Office*